US012697369B2

(12) United States Patent
Liu et al.

(10) Patent No.: US 12,697,369 B2
(45) Date of Patent: Aug. 4, 2026

(54) TARGETING CD24-SIGLEC INTERACTIONS FOR THE TREATMENT OF NONVIRAL HEPATITIS AND LIVER FIBROSIS

(71) Applicants:OncoImmune, Inc., Rockville, MD (US); University of Maryland, Baltimore, Baltimore, MD (US)

(72) Inventors: Yang Liu, Washington, DC (US); Pan Zheng, Washington, DC (US); Xu Wang, Washington, DC (US); Mingyue Liu, Washington, DC (US); Martin Devenport, Gaithersburg, MD (US)

(73) Assignees: ONCOIMMUNE, INC., Rockville, MD (US); UNIVERSITY OF MARYLAND, BALTIMORE, Baltimore, MD (US)

( * ) Notice: Subject to any disclaimer, the term of this patent is extended or adjusted under 35 U.S.C. 154(b) by 1279 days.

(21) Appl. No.: 17/428,769

(22) PCT Filed: Feb. 5, 2020

(86) PCT No.: PCT/US2020/016881
§ 371 (c)(1),
(2) Date: Aug. 5, 2021

(87) PCT Pub. No.: WO2020/163529
PCT Pub. Date: Aug. 13, 2020

(65) Prior Publication Data
US 2022/0000973 A1 Jan. 6, 2022

Related U.S. Application Data

(60) Provisional application No. 62/801,986, filed on Feb. 6, 2019.

(51) Int. Cl.
| | |
|---|---|
| *A61K 38/17* | (2006.01) |
| *A61K 47/68* | (2017.01) |
| *A61P 1/16* | (2006.01) |
| *A61P 3/04* | (2006.01) |
| *C07K 14/705* | (2006.01) |

(52) U.S. Cl.
CPC ........ *A61K 38/177* (2013.01); *A61K 38/1774* (2013.01); *A61K 47/6811* (2017.08); *A61P 1/16* (2018.01); *A61P 3/04* (2018.01); *C07K 14/70596* (2013.01); *C07K 2319/30* (2013.01)

(58) Field of Classification Search
None
See application file for complete search history.

(56) References Cited

U.S. PATENT DOCUMENTS

| | | |
|---|---|---|
| 2013/0231464 A1 | 9/2013 | Zheng et al. |
| 2018/0110828 A1 | 4/2018 | Liu et al. |

FOREIGN PATENT DOCUMENTS

| | | |
|---|---|---|
| CA | 2902727 A1 | 9/2014 |
| WO | 2010102112 A2 | 9/2010 |
| WO | WO 2016/205567 A1 | 12/2016 |
| WO | 2017136492 A1 | 8/2017 |
| WO | 2018217659 A1 | 11/2018 |

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Skolnick et al. (2000). Trends in Biotech. 18(1):34-39.*
Xiaodong GE et al: "High Mobility Group Box-1 Drives Fibrosis Progression Signaling via the Receptor for Advanced Glycation End Products in Mice", Hepatology, John Wiley & Sons, Inc, US, vol. 68, No. 6, Nov. 13, 2018 pp. 2380-2404.
Rogero Marcelo et al: "Obesity, Inflammation, Toll-Like Receptor 4 and Fatty Acids", Nutrients, vol. 10, No. 4, Mar. 30, 2018, p. 432.
Liang Li et al: "Nuclear Factor High-Mobility Group Box 1 Mediating the Activation of Toll-Like Receptor 4 Signaling in Hepatocytes in the Early Stage of Nonalcoholic Fatty Liver Disease in Mice", Hepatology, John Wiley & Sons, Inc, US, vol. 54, No. 5, Jul. 25, 2011, pp. 1620-1630.
Sasa Chu et al: "The Fab Fragment of a Human Anti-Siglec-9 Monoclonal Antibody Suppresses LPS-Induced Inflammatory Responses in Human Macrophages", Frontiers in Immunol, vol. 7, Dec. 26, 2016, pp. 1-12.
Gaskell Harriet et al: "High-Mobility Group Box-1 and Liver Disease", Hepatology Communications, vol. 2, No. 9, Sep. 1, 2018, pp. 1005-1020.
Safer Zadeh Elika et al: "The Liver Disease of Lipodystrophy: The Long Term Effect of Leptin Treatment", Journal of Hepatology, Elsevier, Amsterdam, NL, vol. 59, No. 1, Feb. 21, 2013, pp. 131-137.
Roland B. Walter et al: "ITIM-Dependent Endocytosis of CD33-Related Siglecs: Role of Intracellular Domain, Tyrosine Phosphorylation, and the Tyrosine Phosphatases, Shp1 and Shp2", Journal of Leukocyte Biology, vol. 83, No. 1, Jan. 1, 2008, pp. 200-211.
Chen Guo-Yun et al: "Broad and Direct Interaction Between TLR and Siglec Families of Pattern Recognition Receptors and its Regulation by Neu1", Author Response: Broad and Direct Interaction Between TLR and Siglec Families of Pattern Recognition Receptors and Its Regulation by NEU1, Sep. 3, 2014, XP055970440, Retrieved from the Internet: URL: https://www.ncbi.nlm.nih.gov/pmc/articles/PMC4168287/pdf/elife04066.pdf> * Fig. 1 *.

(Continued)

*Primary Examiner* — Christine J Saoud
*Assistant Examiner* — Jon M Lockard
(74) *Attorney, Agent, or Firm* — Nevrivy Patent Law Group P.L.L.C.

(57) ABSTRACT

Provided herein are methods and compositions for the prevention and treatment of nonalcoholic steatohepatitis (NASH) by targeting the CD24-Siglec axis.

22 Claims, 31 Drawing Sheets
Specification includes a Sequence Listing.

(56)  References Cited

OTHER PUBLICATIONS

Extended European Search Report dated Oct. 25, 2022, for Application No. EP 20752440.6, filed Sep. 6, 2021, as a 371 National Stage Application of PCT/US2020/016881 having an International Filing Date of May 5, 2020.

International Search Report and Written Opinion, PCT/US2020/016881, Date of Mailing: Jun. 23, 2021, 13 pages.

* cited by examiner

FIG. 1A

MGRAMVARLGLGLLLLALLLPTQIYSSETTTGTSSNSSQSTSNSGLAP

NPTNATTKPKSCDKTHTCPPCPAPELLGGPSVFLFPPKPKDTLMISRT

PEVTCVVVDVSHEDPEVKFNWYVDGVEVHNAKTKPREEQYNSTYRVVS

VLTVLHQDWLNGKEYKCKVSNKALPAPIEKTISKAKGQPREPQVYTLP

PSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK

FIG. 1B

MGRAMVARLGLGLLLLALLLPTQIYSSETTTGTSSNSSQSTSNSGLAP

NPTNATTKVPKSCDKTHTCPPCPAPELLGGPSVFLFPPKPKDTLMISR

TPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTL

PPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK

FIG. 1C

MGRAMVARLGLGLLLLALLLPTQIYSSETTTGTSSNSSQSTSNSGLAP

NPTNATTKAPKSCDKTHTCPPCPAPELLGGPSVFLFPPKPKDTLMISR

TPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTL

PPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK

FIG. 2

```
Mouse CD24  NQTSVAPFPGN--QNISAS----PNPTNATTRG
            _*  _     *  *  * *     ********__
Human CD24  SETTTGTSS-NSSQSTSNS-GLAPNPTNATTKA(V)
```

Figures 3A, 3B, 3C:
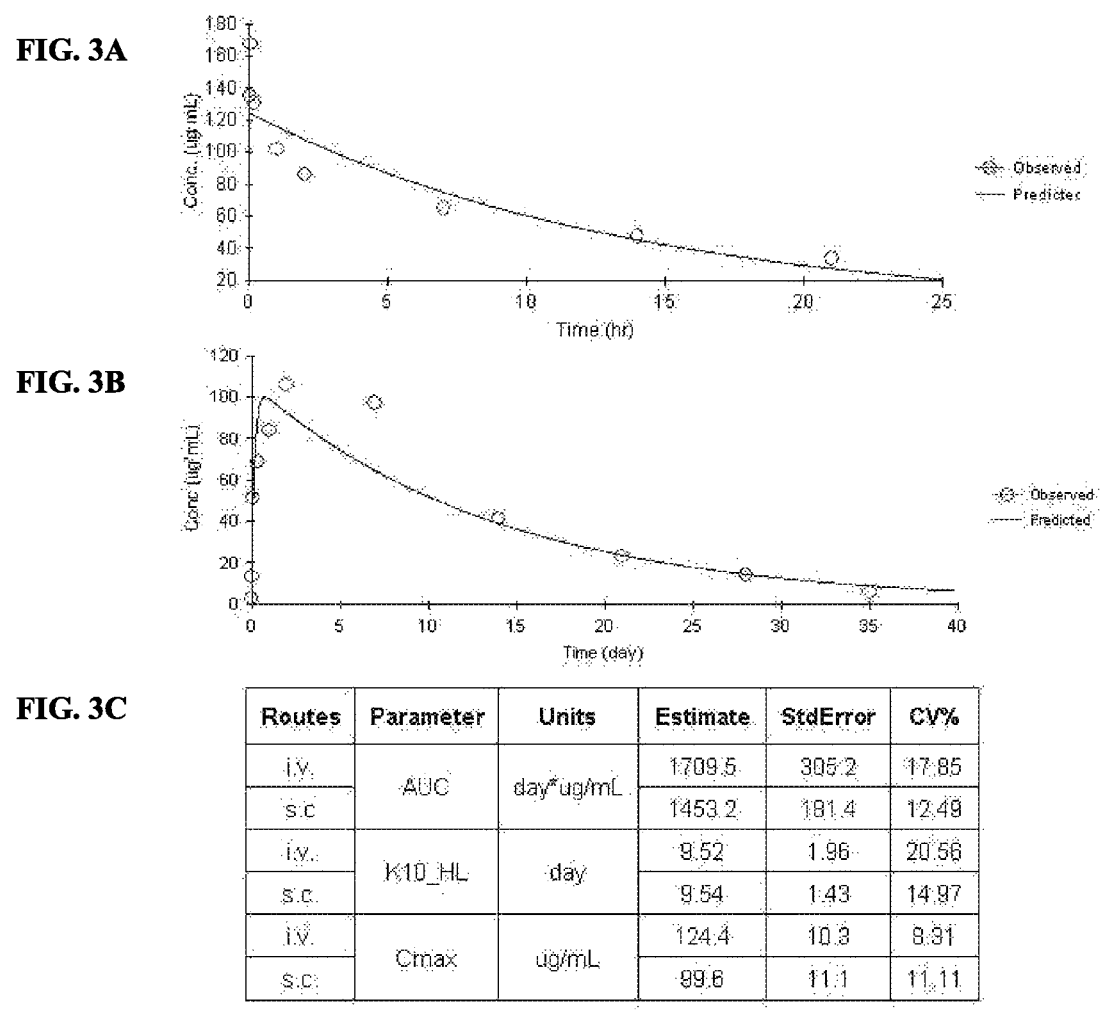

| Routes | Parameter | Units | Estimate | StdError | CV% |
|---|---|---|---|---|---|
| i.v. | AUC | day*ug/mL | 1709.5 | 305.2 | 17.85 |
| s.c | | | 1453.2 | 181.4 | 12.49 |
| i.v. | K10_HL | day | 9.52 | 1.96 | 20.56 |
| s.c. | | | 9.54 | 1.43 | 14.97 |
| i.v. | Cmax | ug/mL | 124.4 | 10.3 | 8.31 |
| s.c. | | | 99.6 | 11.1 | 11.11 |

Day -1
(pre-treatment)

Day 3
(post-treatment)

FIG. 12A
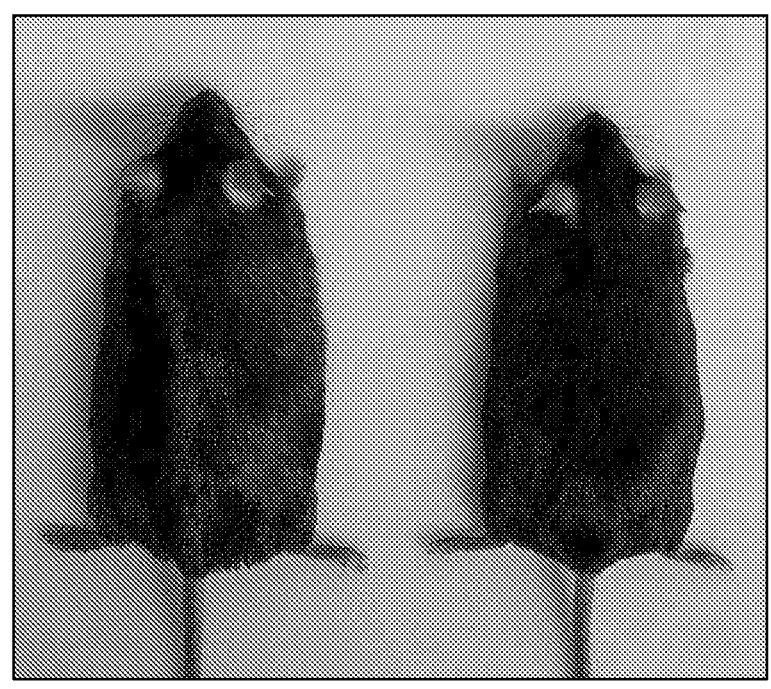

FIG. 12B
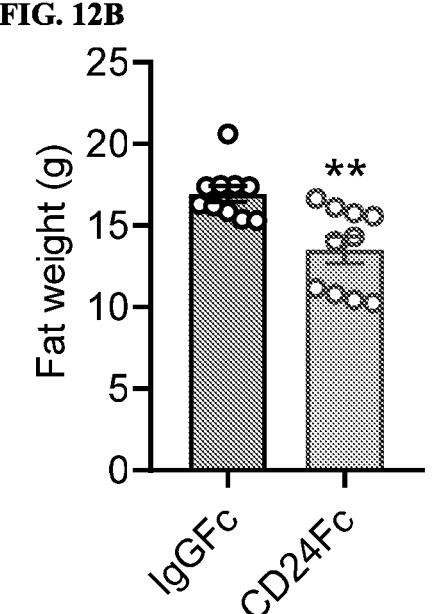
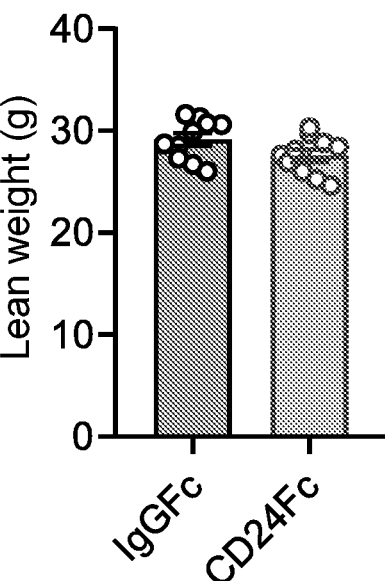

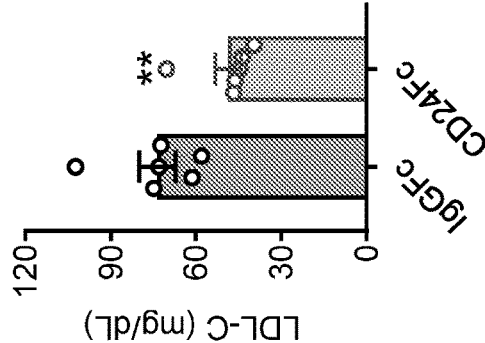
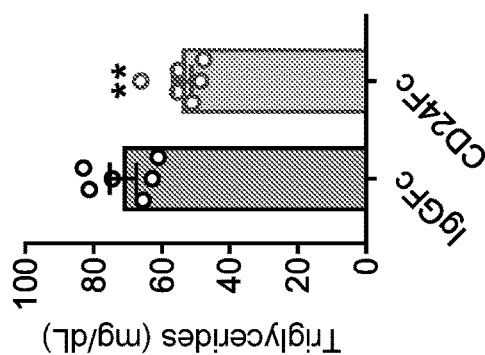
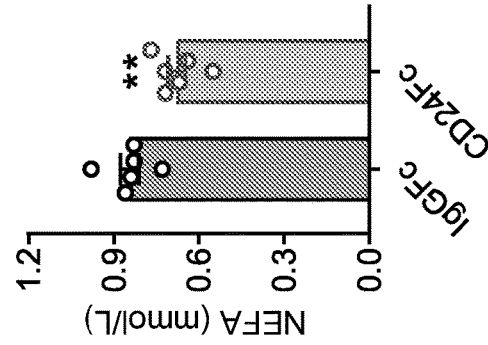
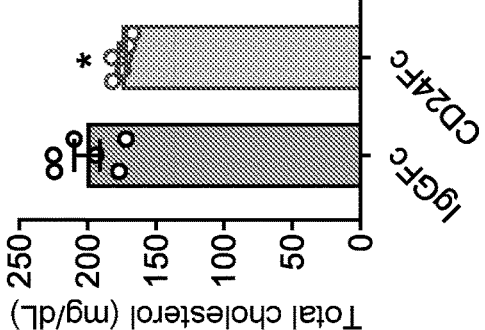
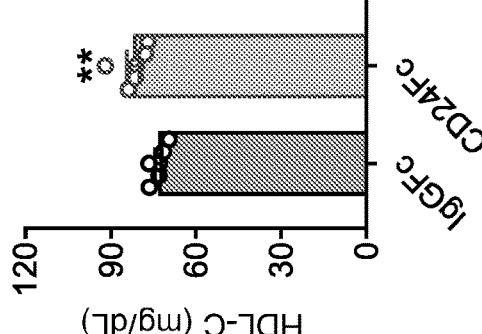
FIG. 12C

Time after glucose injection (min)    Time after insulin injection (min)

FIG. 12F
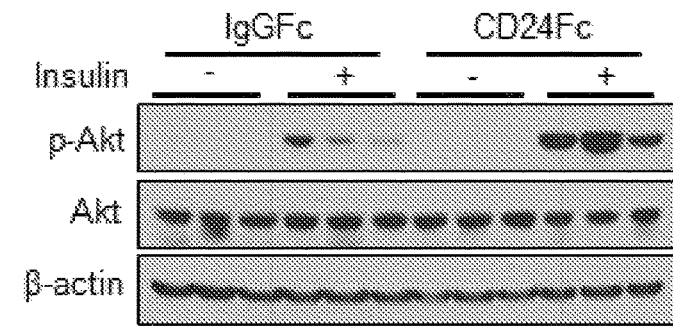
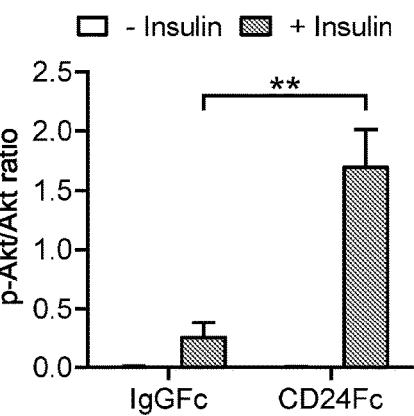
FIG. 12G
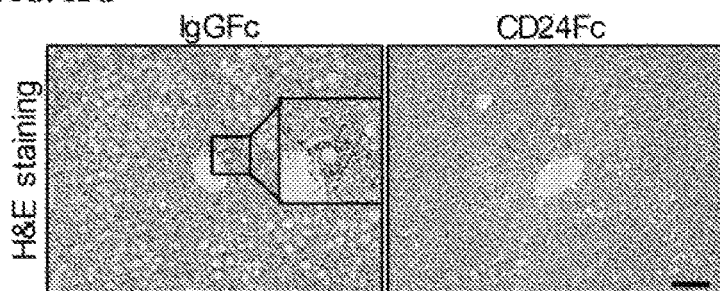
FIG. 12H
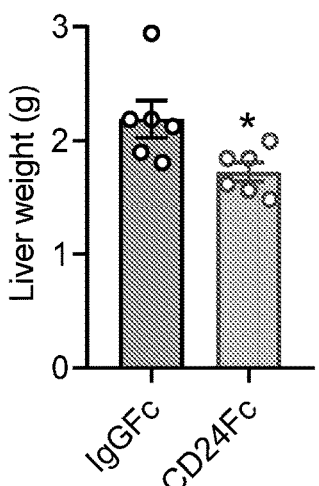

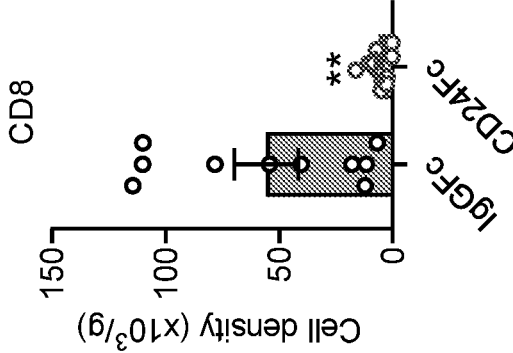
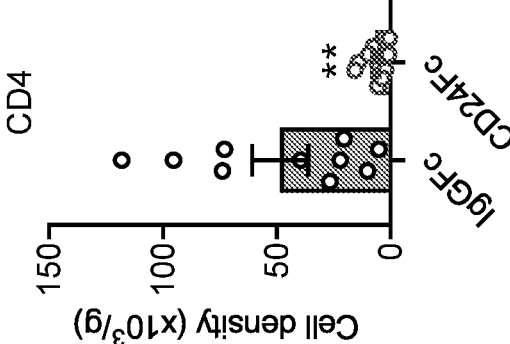
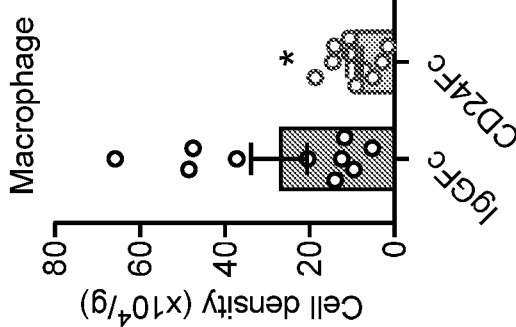
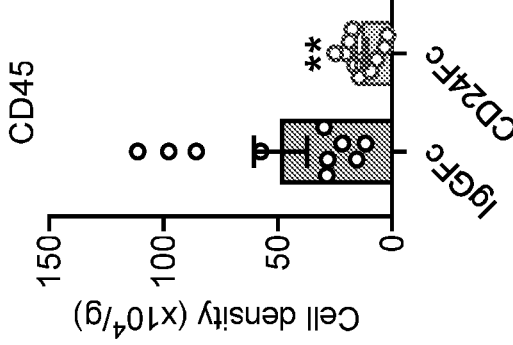
FIG. 12L

FIG. 12M
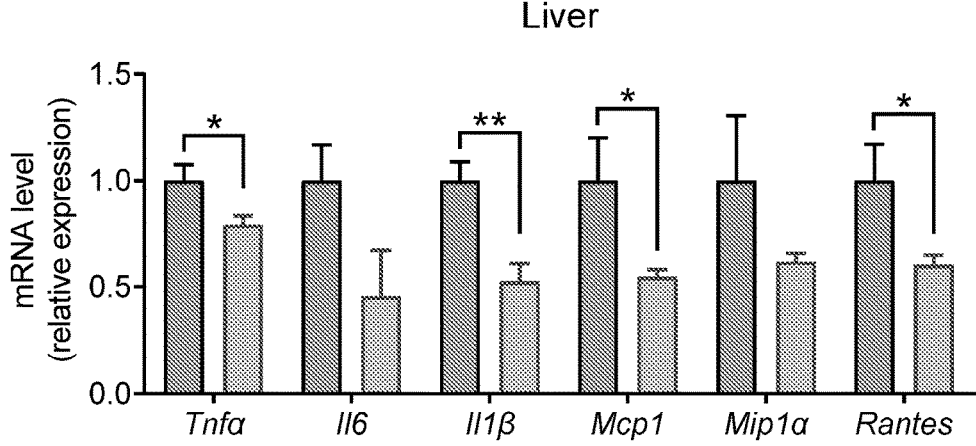
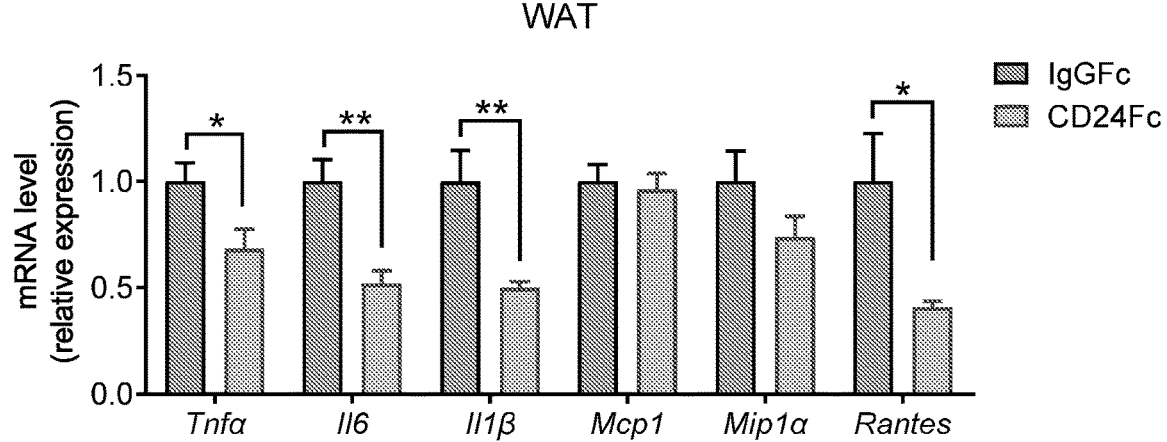

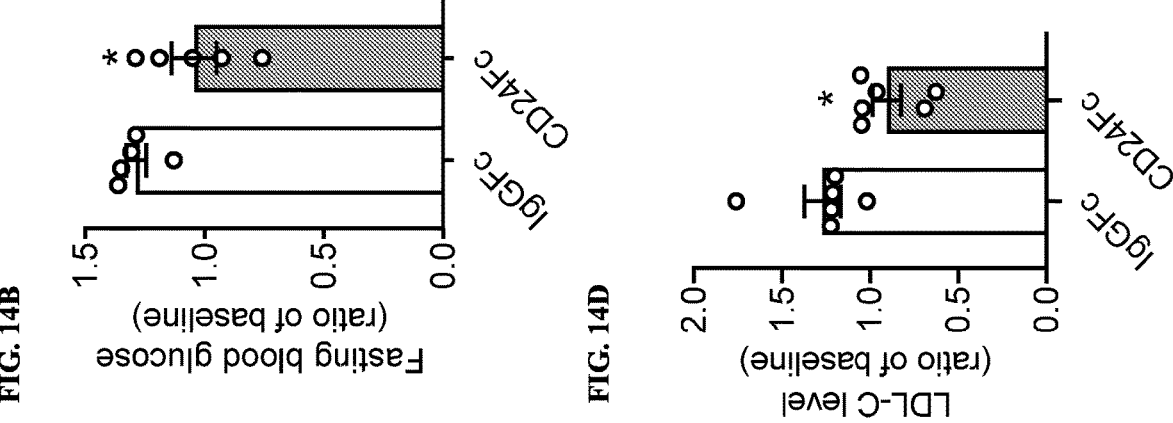
FIG. 14A
FIG. 14B
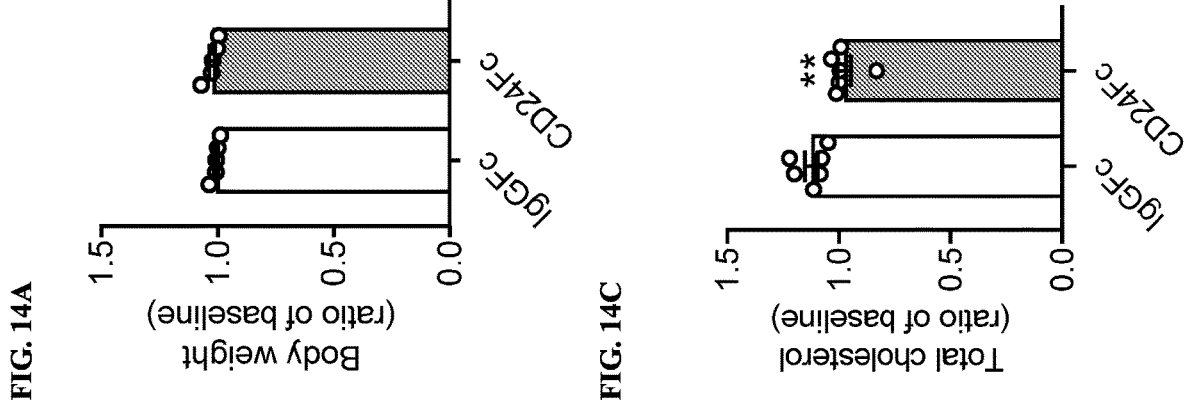
FIG. 14C
FIG. 14D

FIG. 17C
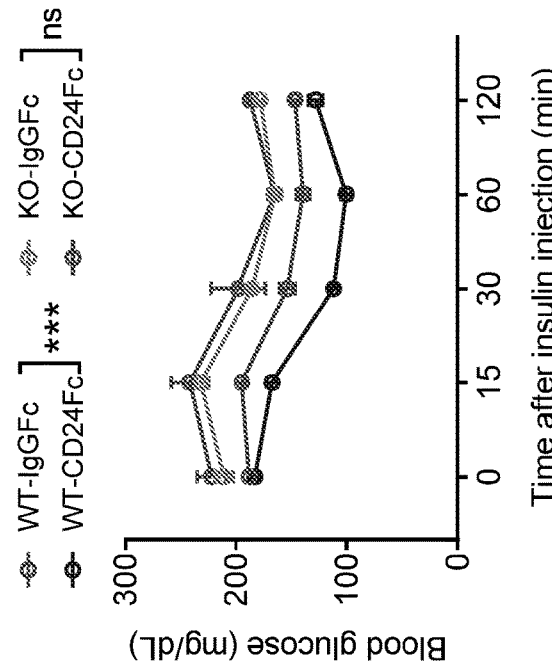
FIG. 17D
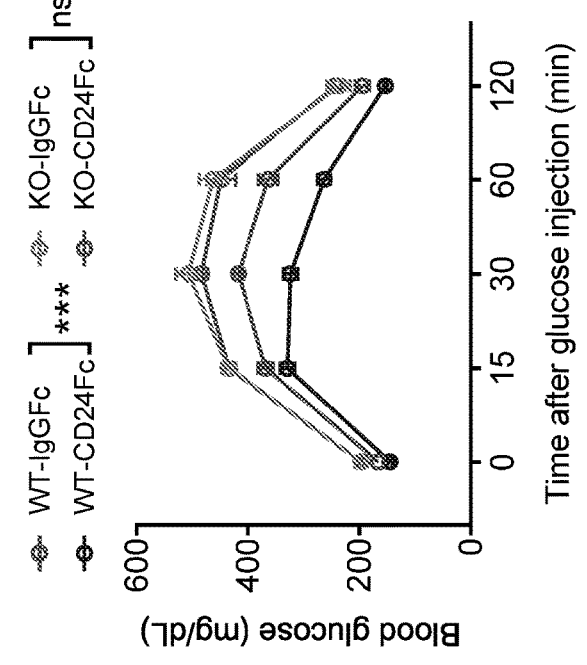
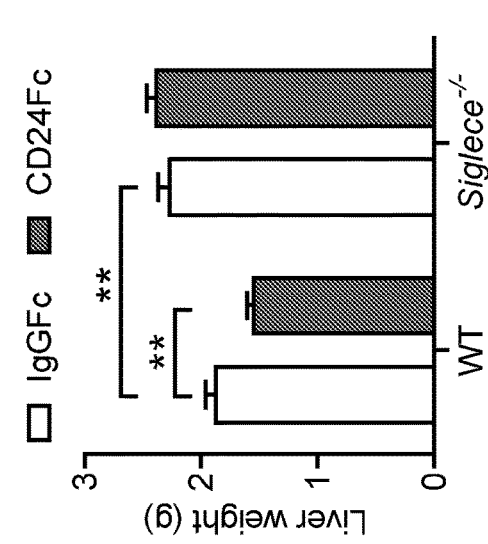

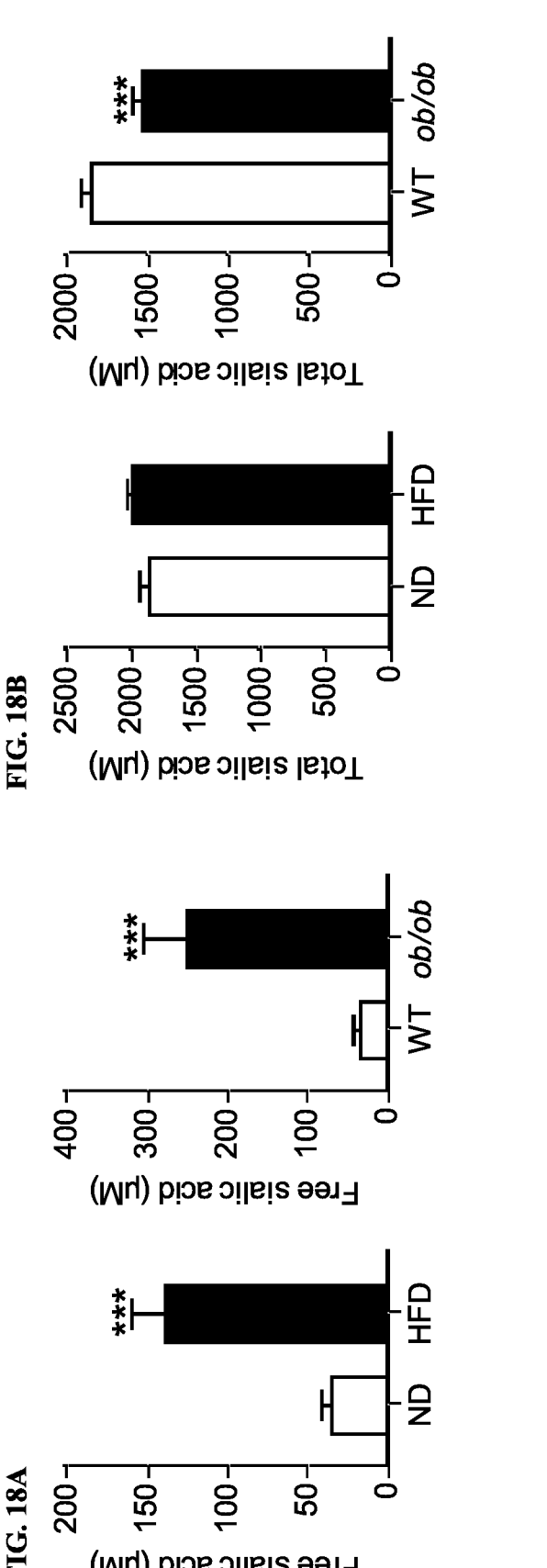
FIG. 18A
FIG. 18B
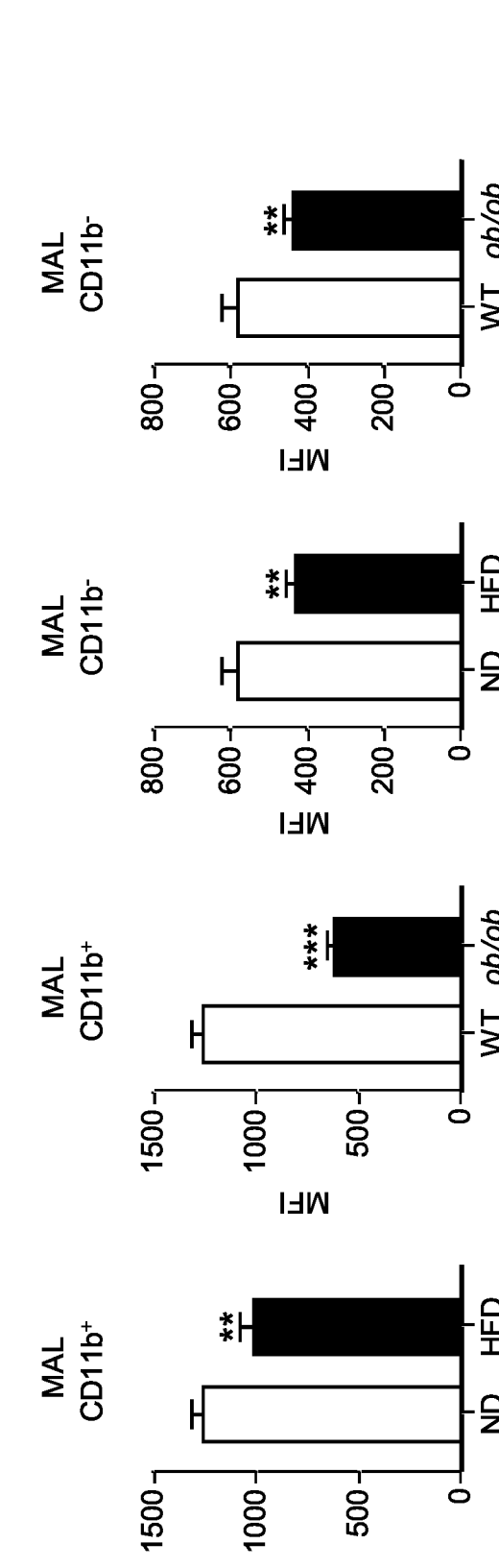
FIG. 18C

SEQUENCE LISTING

```
<160> NUMBER OF SEQ ID NOS: 12

<210> SEQ ID NO 1
<211> LENGTH: 31
<212> TYPE: PRT
<213> ORGANISM: Homo sapiens
<220> FEATURE:
<221> NAME/KEY: VARIANT
<222> LOCATION: (31)..(31)
<223> OTHER INFORMATION: Valine or Alanine

<400> SEQUENCE: 1

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys Xaa
            20                  25                  30

<210> SEQ ID NO 2
<211> LENGTH: 30
<212> TYPE: PRT
<213> ORGANISM: Homo sapiens

<400> SEQUENCE: 2

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys
            20                  25                  30

<210> SEQ ID NO 3
<211> LENGTH: 27
<212> TYPE: PRT
<213> ORGANISM: Mus musculus

<400> SEQUENCE: 3

Asn Gln Thr Ser Val Ala Pro Phe Pro Gly Asn Gln Asn Ile Ser Ala
1               5                   10                  15

Ser Pro Asn Pro Thr Asn Ala Thr Thr Arg Gly
            20                  25

<210> SEQ ID NO 4
<211> LENGTH: 26
<212> TYPE: PRT
<213> ORGANISM: Homo sapiens

<400> SEQUENCE: 4

Met Gly Arg Ala Met Val Ala Arg Leu Gly Leu Gly Leu Leu Leu Leu
1               5                   10                  15

Ala Leu Leu Leu Pro Thr Gln Ile Tyr Ser
            20                  25

<210> SEQ ID NO 5
<211> LENGTH: 287
<212> TYPE: PRT
<213> ORGANISM: Artificial
<220> FEATURE:
<223> OTHER INFORMATION: Fusion protein

<400> SEQUENCE: 5
```

-continued

```
Met Gly Arg Ala Met Val Ala Arg Leu Gly Leu Gly Leu Leu Leu Leu
1               5                   10                  15

Ala Leu Leu Leu Pro Thr Gln Ile Tyr Ser Ser Glu Thr Thr Thr Gly
                20                  25                  30

Thr Ser Ser Asn Ser Ser Gln Ser Thr Ser Asn Ser Gly Leu Ala Pro
        35                  40                  45

Asn Pro Thr Asn Ala Thr Thr Lys Pro Lys Ser Cys Asp Lys Thr His
    50                  55                  60

Thr Cys Pro Pro Cys Pro Ala Pro Glu Leu Leu Gly Gly Pro Ser Val
65                  70                  75                  80

Phe Leu Phe Pro Pro Lys Pro Lys Asp Thr Leu Met Ile Ser Arg Thr
                85                  90                  95

Pro Glu Val Thr Cys Val Val Val Asp Val Ser His Glu Asp Pro Glu
            100                 105                 110

Val Lys Phe Asn Trp Tyr Val Asp Gly Val Glu Val His Asn Ala Lys
        115                 120                 125

Thr Lys Pro Arg Glu Glu Gln Tyr Asn Ser Thr Tyr Arg Val Val Ser
    130                 135                 140

Val Leu Thr Val Leu His Gln Asp Trp Leu Asn Gly Lys Glu Tyr Lys
145                 150                 155                 160

Cys Lys Val Ser Asn Lys Ala Leu Pro Ala Pro Ile Glu Lys Thr Ile
            165                 170                 175

Ser Lys Ala Lys Gly Gln Pro Arg Glu Pro Gln Val Tyr Thr Leu Pro
            180                 185                 190

Pro Ser Arg Asp Glu Leu Thr Lys Asn Gln Val Ser Leu Thr Cys Leu
            195                 200                 205

Val Lys Gly Phe Tyr Pro Ser Asp Ile Ala Val Glu Trp Glu Ser Asn
            210                 215                 220

Gly Gln Pro Glu Asn Asn Tyr Lys Thr Thr Pro Pro Val Leu Asp Ser
225                 230                 235                 240

Asp Gly Ser Phe Phe Leu Tyr Ser Lys Leu Thr Val Asp Lys Ser Arg
                245                 250                 255

Trp Gln Gln Gly Asn Val Phe Ser Cys Ser Val Met His Glu Ala Leu
            260                 265                 270

His Asn His Tyr Thr Gln Lys Ser Leu Ser Leu Ser Pro Gly Lys
            275                 280                 285
```

<210> SEQ ID NO 6
<211> LENGTH: 261
<212> TYPE: PRT
<213> ORGANISM: Artificial
<220> FEATURE:
<223> OTHER INFORMATION: Fusion protein

<400> SEQUENCE: 6

```
Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys Pro Lys
                20                  25                  30

Ser Cys Asp Lys Thr His Thr Cys Pro Pro Cys Pro Ala Pro Glu Leu
        35                  40                  45

Leu Gly Gly Pro Ser Val Phe Leu Phe Pro Pro Lys Pro Lys Asp Thr
        50                  55                  60

Leu Met Ile Ser Arg Thr Pro Glu Val Thr Cys Val Val Val Asp Val
65                  70                  75                  80
```

```
Ser His Glu Asp Pro Glu Val Lys Phe Asn Trp Tyr Val Asp Gly Val
                85                  90                  95

Glu Val His Asn Ala Lys Thr Lys Pro Arg Glu Glu Gln Tyr Asn Ser
            100                 105                 110

Thr Tyr Arg Val Val Ser Val Leu Thr Val Leu His Gln Asp Trp Leu
        115                 120                 125

Asn Gly Lys Glu Tyr Lys Cys Lys Val Ser Asn Lys Ala Leu Pro Ala
    130                 135                 140

Pro Ile Glu Lys Thr Ile Ser Lys Ala Lys Gly Gln Pro Arg Glu Pro
145                 150                 155                 160

Gln Val Tyr Thr Leu Pro Pro Ser Arg Asp Glu Leu Thr Lys Asn Gln
                165                 170                 175

Val Ser Leu Thr Cys Leu Val Lys Gly Phe Tyr Pro Ser Asp Ile Ala
                180                 185                 190

Val Glu Trp Glu Ser Asn Gly Gln Pro Glu Asn Asn Tyr Lys Thr Thr
            195                 200                 205

Pro Pro Val Leu Asp Ser Asp Gly Ser Phe Phe Leu Tyr Ser Lys Leu
    210                 215                 220

Thr Val Asp Lys Ser Arg Trp Gln Gln Gly Asn Val Phe Ser Cys Ser
225                 230                 235                 240

Val Met His Glu Ala Leu His Asn His Tyr Thr Gln Lys Ser Leu Ser
            245                 250                 255

Leu Ser Pro Gly Lys
            260

<210> SEQ ID NO 7
<211> LENGTH: 231
<212> TYPE: PRT
<213> ORGANISM: Homo sapiens

<400> SEQUENCE: 7

Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
        130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
```

```
                180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230
```

<210> SEQ ID NO 8
<211> LENGTH: 288
<212> TYPE: PRT
<213> ORGANISM: Artificial
<220> FEATURE:
<223> OTHER INFORMATION: Fusion protein

<400> SEQUENCE: 8

```
Met Gly Arg Ala Met Val Ala Arg Leu Gly Leu Gly Leu Leu Leu Leu
1               5                   10                  15

Ala Leu Leu Leu Pro Thr Gln Ile Tyr Ser Ser Glu Thr Thr Thr Gly
            20                  25                  30

Thr Ser Ser Asn Ser Ser Gln Ser Thr Ser Asn Ser Gly Leu Ala Pro
        35                  40                  45

Asn Pro Thr Asn Ala Thr Thr Lys Val Pro Lys Ser Cys Asp Lys Thr
    50                  55                  60

His Thr Cys Pro Pro Cys Pro Ala Pro Glu Leu Leu Gly Gly Pro Ser
65                  70                  75                  80

Val Phe Leu Phe Pro Pro Lys Pro Lys Asp Thr Leu Met Ile Ser Arg
                85                  90                  95

Thr Pro Glu Val Thr Cys Val Val Val Asp Val Ser His Glu Asp Pro
            100                 105                 110

Glu Val Lys Phe Asn Trp Tyr Val Asp Gly Val Glu Val His Asn Ala
        115                 120                 125

Lys Thr Lys Pro Arg Glu Glu Gln Tyr Asn Ser Thr Tyr Arg Val Val
    130                 135                 140

Ser Val Leu Thr Val Leu His Gln Asp Trp Leu Asn Gly Lys Glu Tyr
145                 150                 155                 160

Lys Cys Lys Val Ser Asn Lys Ala Leu Pro Ala Pro Ile Glu Lys Thr
                165                 170                 175

Ile Ser Lys Ala Lys Gly Gln Pro Arg Glu Pro Gln Val Tyr Thr Leu
            180                 185                 190

Pro Pro Ser Arg Asp Glu Leu Thr Lys Asn Gln Val Ser Leu Thr Cys
        195                 200                 205

Leu Val Lys Gly Phe Tyr Pro Ser Asp Ile Ala Val Glu Trp Glu Ser
    210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Lys Leu Thr Val Asp Lys Ser
                245                 250                 255

Arg Trp Gln Gln Gly Asn Val Phe Ser Cys Ser Val Met His Glu Ala
            260                 265                 270

Leu His Asn His Tyr Thr Gln Lys Ser Leu Ser Leu Ser Pro Gly Lys
        275                 280                 285
```

<210> SEQ ID NO 9
<211> LENGTH: 288
<212> TYPE: PRT

-continued

<213> ORGANISM: Artificial
<220> FEATURE:
<223> OTHER INFORMATION: Fusion protein

<400> SEQUENCE: 9

Met Gly Arg Ala Met Val Ala Arg Leu Gly Leu Gly Leu Leu Leu Leu
1               5                   10                  15

Ala Leu Leu Leu Pro Thr Gln Ile Tyr Ser Ser Glu Thr Thr Thr Gly
            20                  25                  30

Thr Ser Ser Asn Ser Ser Gln Ser Thr Ser Asn Ser Gly Leu Ala Pro
        35                  40                  45

Asn Pro Thr Asn Ala Thr Thr Lys Ala Pro Lys Ser Cys Asp Lys Thr
    50                  55                  60

His Thr Cys Pro Pro Cys Pro Ala Pro Glu Leu Leu Gly Gly Pro Ser
65                  70                  75                  80

Val Phe Leu Phe Pro Pro Lys Pro Lys Asp Thr Leu Met Ile Ser Arg
                85                  90                  95

Thr Pro Glu Val Thr Cys Val Val Val Asp Val Ser His Glu Asp Pro
            100                 105                 110

Glu Val Lys Phe Asn Trp Tyr Val Asp Gly Val Glu Val His Asn Ala
        115                 120                 125

Lys Thr Lys Pro Arg Glu Glu Gln Tyr Asn Ser Thr Tyr Arg Val Val
    130                 135                 140

Ser Val Leu Thr Val Leu His Gln Asp Trp Leu Asn Gly Lys Glu Tyr
145                 150                 155                 160

Lys Cys Lys Val Ser Asn Lys Ala Leu Pro Ala Pro Ile Glu Lys Thr
                165                 170                 175

Ile Ser Lys Ala Lys Gly Gln Pro Arg Glu Pro Gln Val Tyr Thr Leu
            180                 185                 190

Pro Pro Ser Arg Asp Glu Leu Thr Lys Asn Gln Val Ser Leu Thr Cys
        195                 200                 205

Leu Val Lys Gly Phe Tyr Pro Ser Asp Ile Ala Val Glu Trp Glu Ser
    210                 215                 220

Asn Gly Gln Pro Glu Asn Asn Tyr Lys Thr Thr Pro Pro Val Leu Asp
225                 230                 235                 240

Ser Asp Gly Ser Phe Phe Leu Tyr Ser Lys Leu Thr Val Asp Lys Ser
                245                 250                 255

Arg Trp Gln Gln Gly Asn Val Phe Ser Cys Ser Val Met His Glu Ala
            260                 265                 270

Leu His Asn His Tyr Thr Gln Lys Ser Leu Ser Leu Ser Pro Gly Lys
        275                 280                 285

<210> SEQ ID NO 10
<211> LENGTH: 29
<212> TYPE: PRT
<213> ORGANISM: Macaca fascicularis

<400> SEQUENCE: 10

Thr Val Thr Thr Ser Ala Pro Leu Ser Ser Asn Ser Pro Gln Asn Thr
1               5                   10                  15

Ser Thr Thr Pro Asn Pro Ala Asn Thr Thr Thr Lys Ala
            20                  25

<210> SEQ ID NO 11
<211> LENGTH: 262
<212> TYPE: PRT
<213> ORGANISM: Artificial

<220> FEATURE:
<223> OTHER INFORMATION: Fusion protein

<400> SEQUENCE: 11

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys Val Pro
            20                  25                  30

Lys Ser Cys Asp Lys Thr His Thr Cys Pro Pro Cys Pro Ala Pro Glu
        35                  40                  45

Leu Leu Gly Gly Pro Ser Val Phe Leu Phe Pro Pro Lys Pro Lys Asp
        50                  55                  60

Thr Leu Met Ile Ser Arg Thr Pro Glu Val Thr Cys Val Val Val Asp
65                  70                  75                  80

Val Ser His Glu Asp Pro Glu Val Lys Phe Asn Trp Tyr Val Asp Gly
            85                  90                  95

Val Glu Val His Asn Ala Lys Thr Lys Pro Arg Glu Glu Gln Tyr Asn
            100                 105                 110

Ser Thr Tyr Arg Val Val Ser Val Leu Thr Val Leu His Gln Asp Trp
        115                 120                 125

Leu Asn Gly Lys Glu Tyr Lys Cys Lys Val Ser Asn Lys Ala Leu Pro
        130                 135                 140

Ala Pro Ile Glu Lys Thr Ile Ser Lys Ala Lys Gly Gln Pro Arg Glu
145                 150                 155                 160

Pro Gln Val Tyr Thr Leu Pro Pro Ser Arg Asp Glu Leu Thr Lys Asn
            165                 170                 175

Gln Val Ser Leu Thr Cys Leu Val Lys Gly Phe Tyr Pro Ser Asp Ile
            180                 185                 190

Ala Val Glu Trp Glu Ser Asn Gly Gln Pro Glu Asn Asn Tyr Lys Thr
            195                 200                 205

Thr Pro Pro Val Leu Asp Ser Asp Gly Ser Phe Phe Leu Tyr Ser Lys
        210                 215                 220

Leu Thr Val Asp Lys Ser Arg Trp Gln Gln Gly Asn Val Phe Ser Cys
225                 230                 235                 240

Ser Val Met His Glu Ala Leu His Asn His Tyr Thr Gln Lys Ser Leu
            245                 250                 255

Ser Leu Ser Pro Gly Lys
            260

<210> SEQ ID NO 12
<211> LENGTH: 262
<212> TYPE: PRT
<213> ORGANISM: Artificial
<220> FEATURE:
<223> OTHER INFORMATION: Fusion protein

<400> SEQUENCE: 12

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys Ala Pro
            20                  25                  30

Lys Ser Cys Asp Lys Thr His Thr Cys Pro Pro Cys Pro Ala Pro Glu
        35                  40                  45

Leu Leu Gly Gly Pro Ser Val Phe Leu Phe Pro Pro Lys Pro Lys Asp
        50                  55                  60

Thr Leu Met Ile Ser Arg Thr Pro Glu Val Thr Cys Val Val Val Asp

-continued

```
65                    70                    75                    80

Val Ser His Glu Asp Pro Glu Val Lys Phe Asn Trp Tyr Val Asp Gly
                85                    90                    95

Val Glu Val His Asn Ala Lys Thr Lys Pro Arg Glu Glu Gln Tyr Asn
                100                   105                   110

Ser Thr Tyr Arg Val Val Ser Val Leu Thr Val Leu His Gln Asp Trp
            115                   120                   125

Leu Asn Gly Lys Glu Tyr Lys Cys Lys Val Ser Asn Lys Ala Leu Pro
        130                   135                   140

Ala Pro Ile Glu Lys Thr Ile Ser Lys Ala Lys Gly Gln Pro Arg Glu
145                   150                   155                   160

Pro Gln Val Tyr Thr Leu Pro Pro Ser Arg Asp Glu Leu Thr Lys Asn
                165                   170                   175

Gln Val Ser Leu Thr Cys Leu Val Lys Gly Phe Tyr Pro Ser Asp Ile
                180                   185                   190

Ala Val Glu Trp Glu Ser Asn Gly Gln Pro Glu Asn Asn Tyr Lys Thr
                195                   200                   205

Thr Pro Pro Val Leu Asp Ser Asp Gly Ser Phe Phe Leu Tyr Ser Lys
        210                   215                   220

Leu Thr Val Asp Lys Ser Arg Trp Gln Gln Gly Asn Val Phe Ser Cys
225                   230                   235                   240

Ser Val Met His Glu Ala Leu His Asn His Tyr Thr Gln Lys Ser Leu
                245                   250                   255

Ser Leu Ser Pro Gly Lys
                260
```

TARGETING CD24-SIGLEC INTERACTIONS FOR THE TREATMENT OF NONVIRAL HEPATITIS AND LIVER FIBROSIS

CROSS-REFERENCE TO RELATED APPLICATIONS

The present application is a U.S.C. § 371 national phase application of PCT International Application No. PCT/US2020/016881, filed Feb. 5, 2020, which claims priority to U.S. Provisional Patent Application No. 62/801,986, filed Feb. 6, 2019. The disclosures of each are incorporated herein by reference in their entireties.

FIELD OF THE INVENTION

This invention relates to the prevention and treatment of nonalcoholic steatohepatitis using CD24 proteins or by targeting CD24-Siglec interactions.

BACKGROUND OF THE INVENTION

Non-alcoholic fatty liver disease (NAFLD) is the most common cause of chronic liver disease in the Western hemisphere and a leading cause of liver-related morbidity and mortality worldwide. NAFLD represents a clinico-pathological spectrum of disease that primarily manifests as excessive accumulation of fat in the hepatocyte (steatosis). It is considered to be the hepatic manifestation of the metabolic syndrome, whose other pathologies include obesity, insulin resistance, hypertension and hyperlipidemia. NAFLD is broadly categorized into 2 phenotypes, namely: non-alcoholic fatty liver (NAFL) which is marked by isolated steatosis, while the more aggressive subtype, non-alcoholic steatohepatitis (NASH), is characterized by cell injury, inflammatory cell infiltration and hepatocyte ballooning that may further progress to fibrosis, cirrhosis, and hepatocellular carcinoma (HCC).

NASH is the most common chronic liver diseases among children, and affects 2-12% of general population. Within the next 5 to 15 years, NASH is expected surpass hepatitis C virus infection as the leading etiology of end-stage liver disease requiring liver transplantation. NASH is characterized by fatty livers with lymphocyte infiltration, and occasionally liver fibrosis, among individuals without excessive alcohol uses. NASH is also a major cause of liver cancer and liver cirrhosis. Although the cause of NASH is not fully understood, it is known to be associated with obesity and other metabolic disorders, such as hyperlipidemia and type II diabetes. Despite the significant burden to the public health system, an effective treatment for NASH is not yet available.

SUMMARY OF THE INVENTION

Provided herein is a method of treating or preventing metabolic diseases including NASH or other types of non-alcoholic fatty liver disease (NAFLD) in a subject. Inflammation is a major factor in the development of metabolic disorders and major inflammatory signaling pathways, such as NF-κB and JNK pathways, have been reported to play crucial roles in the regulation of insulin sensitivity and metabolic homeostasis. However, until now the molecular interactions that regulate chronic inflammation underlying metabolic syndrome remain largely unknown. This invention describes the missing link between inflammation and metabolic syndromes, but also provides a therapeutic approach to treat non-alcoholic fatty liver disease (NAFLD).

The treatment may be for reducing hepatomegaly, steatosis, hepatic lymphocyte infiltration, or focal hepatic fibrosis. The method may comprise administering a CD24 protein or a Siglec agonist to a subject in need thereof. CD24 is a cell surface glycoprotein rich in sialic acid. It has been demonstrated that CD24 interacts with members of the Siglec family of proteins to suppress inflammation caused by tissue injuries, specifically those mediated by damage-associated molecular patterns (DAMPS). Clinical and pre-clinical data demonstrate that CD24Fc has the ability to simultaneously lower serum LDL-C and glucose, while also increasing leptin levels. Since the connection between CD24 and NASH has not been reported, the inventors investigated its function in NASH.

Chronic exposure to high fat diet (HFD) causes moderate non-alcoholic steatosis hepatitis (NASH), with hepatic steatosis, inflammation and mild fibrosis in mice. However, lipid accumulation is largely alleviated by treatment with CD24Fc and, consistent with liver steatosis data, hepatomegaly observed in diet-induced obese (DIO) mice was largely prevented by CD24Fc treatment. Liver fibrosis, a prominent feature in human NASH, is present but generally mild in HFD-fed mice. However, CD24Fc treatment still significantly alleviated the modest hepatic fibrosis induced by HFD feeding. Immune cell infiltrates, another key hallmark of NASH, were also markedly decreased in liver and adipose tissues in CD24Fc-treated mice. Consistently, there was a significant attenuation in the levels of mRNAs encoding key inflammatory cytokines in liver and adipose tissues in CD24Fc-treated mice.

Using CD24 knockout mice and mice fed on high fat diets, the inventors have demonstrated that the CD24 pathway can suppress the development of mice and that CD24Fc has the ability to attenuate high fat-diet induced NASH, including hepatomegaly and fibrosis.

In addition to binding to Siglec G (Siglec 10 in human), CD24Fc was found to bind to mouse Siglec E. Furthermore, Siglece$^{-/-}$ mice showed increased weight gain due to fat content, impaired glucose and lipid homeostasis, as indicated by remarkably increased fasting blood glucose, LDL-C and TC levels, which recapitulate the CD24 knockout phenotype. Additionally, Siglec-E deficiency led to an impaired glucose tolerance and insulin sensitivity, and Siglece$^{-/-}$ mice exhibited hepatic steatosis and increased liver size, with a significant increase in lipid accumulation and liver fibrosis. All of these findings illustrate that Siglec-E deficiency aggravates diet-induced metabolic syndrome and indicate a role of the CD24-Siglec-E axis in the regulation of obesity-related metabolic disorders. Significantly, Siglece$^{-/-}$ mice do not respond to CD24Fc treatment demonstrating that the therapeutic function of CD24Fc for metabolic syndrome in mice is mediated specifically through Siglec-E.

Chronic inflammation is a major underlying cause for metabolic disorders. Most Siglecs are considered to be negative regulators of the immune response and inflammation as they contain cytosolic immune receptor tyrosine-based inhibitory motifs (ITIMs). Both Cd24- and Siglece-deficient mice show higher levels of inflammatory cytokines in serum, such as TNF-α and IL-6, and more immune cell infiltrates in the liver and adipose tissues. Meanwhile, the expression of mRNAs encoding several key inflammatory cytokines and chemokines are significantly increased in the liver and adipose tissues from Cd24$^-$ or Siglece$^{-/-}$ mice compared to WT controls.

Therefore, targeted mutations of the CD24 and Siglece genes in mice cause, while CD24Fc treatment reduces in Siglece-dependent manner, metabolic disorders in mice, including hyperlipidemia, hyperglycosemia and insulin resistance as well as non-alcoholic steatosis hepatitis.

Taken together, the data demonstrate that CD24Fc treatment suppresses steatosis, focal inflammation and liver fibrosis, all of which are defining features of NASH. Therefore, CD24Fc is valuable for treating or preventing NASH or other NAFLDs.

Provided herein is a method of treating or preventing nonalcoholic steatohepatitis, liver steatosis, nonviral hepatitis, focal inflammation of the liver, or liver fibrosis in a subject in need thereof. The method may comprise administering a CD24 protein or Siglec agonist to the subject. The subject may not have a history of excessive alcohol use.

The CD24 protein may comprise a mature human CD24 polypeptide or a variant thereof. The mature human CD24 polypeptide may comprise the sequence set forth in SEQ ID NO: 1 or 2. The CD24 protein may comprise a protein tag. The protein tag may be fused at the N- or C-terminus of the CD24 protein. The protein tag may comprise a portion of a mammalian immunoglobulin (Ig) protein. The portion of the Ig protein may be a Fc region of a human Ig protein. The Fc region may comprise a hinge region and CH2 and CH3 domains of IgG1, IgG2, IgG3, IgG4, or IgA. The Fc region may comprise a hinge region and CH2, CH3 and CH4 domains of IgM. The CD24 protein may comprise the sequence set forth in SEQ ID NO: 6, 11 or 12. The amino acid sequence of the CD24 protein may consist of the sequence set forth in SEQ ID NO: 6, 11 or 12. The CD24 protein may be soluble, and may be glycosylated.

The Siglec agonist may be characterized by its ability to induce association of tyrosine phosphorylation in one or more Immunoreceptor tyrosine-based inhibitor motif (ITIM) domains of a Siglec. The Siglec may be Siglec E or a functional homolog thereof. The functional homolog may be human, and may be one or more of Siglec 6-9 and 12.

BRIEF DESCRIPTION OF THE DRAWINGS

FIG. 1A shows the amino acid composition of the full length CD24 fusion protein, CD24Fc (also referred to herein as CD24Ig) (SEQ ID NO: 5). The underlined 26 amino acids are the signal peptide of CD24 (SEQ ID NO: 4), which are cleaved off during secretion from a cell expressing the protein and thus missing from the processed version of the protein (SEQ ID NO: 6). The bold portion of the sequence is the extracellular domain of the mature CD24 protein used in the fusion protein (SEQ ID NO: 2). The last amino acid (A or V) that is ordinarily present in the mature CD24 protein has been deleted from the construct to avoid immunogenicity. The non-underlined, non-bold letters are the sequence of IgG1 Fc, including the hinge region and CH1 and CH2 domains (SEQ ID NO: 7). FIG. 1B shows the sequence of CD24'Fc (SEQ ID NO: 8), in which the mature human CD24 protein (bold) is the valine polymorphic variant of SEQ ID NO: 1. FIG. 1C shows the sequence of CD24$^4$Fc (SEQ ID NO: 9), in which the mature human CD24 protein (bold) is the alanine polymorphic variant of SEQ ID NO: 1. The various parts of the fusion protein in FIGS. 1B and 1C are marked as in FIG. 1A and the variant valine/alanine amino acid is double underlined.

FIG. 2 shows amino acid sequence variations between mature CD24 proteins from mouse (SEQ ID NO: 3) and human (SEQ ID NO: 2). The potential O-glycosylation sites are bolded, and the N-glycosylation sites are underlined.

FIGS. 3A-C show WinNonlin compartmental modeling analysis of pharmacokinetics of CD24Fc (CD24Ig) in mice. The opened circles represent the average of 3 mice, and the line is the predicted pharmacokinetic curve. FIG. 3A. i.v. injection of 1 mg CD24Fc. FIG. 3B. s.c. injection of 1 mg CD24Fc. FIG. 3C. Comparison of the total amounts of antibody in the blood as measured by areas under curve (AUC), half-life and maximal blood concentration. Note that overall, the AUC and $C_{max}$ of the s.c. injection is about 80% of i.v. injection, although the difference is not statistically significant.

FIG. 5 shows a dose proportionality plot of CD24Fc $C_{max}$ versus dose for a PK Evaluable Population.

FIG. 6 shows a dose proportionality plot of CD24Fc $AUC_{0-42d}$ versus dose for a PK Evaluable Population.

FIG. 10A. Volcano plot showing the gene expression fold change (x axis, log 2 scale) and their p value significance (y axis, −log 10 scale). Significantly differentially expressed genes (P<0.05 and fold change >1.5) are highlighted in red (up-regulated) and blue (down-regulated), with the black dashed lines representing the boundaries for the identification of up- or down-regulated genes. Selected genes related to inflammation are indicated. FIG. 10B Heat map of alterations in expression of inflammatory genes in PBMC from healthy volunteers receiving 240 mg of CD24Fc treatment. FIG. 10C. The mRNA levels of inflammatory genes of PBMC samples from individual patients were examined by real-time PCR. All values are expressed as mean±SEM. *p<0.05, p<0.01, *p<0.001, unpaired Student's t-test (A and B), linear regression analysis (A and B) or paired t-test (C).

FIG. 12 shows that CD24Fc alleviates obesity-related metabolic disorders in DIO mice. Male C57BL/6NCr mice were fed with a high-fat diet and concurrently treated with CD24Fc (100 µg per dose) or IgGFc control twice a week for 8 weeks. FIG. 12A. Body weight and representative photos of mice at the end of final treatment. n=10 per group. FIG. 12B. Body composition was detected by DEXA. n=10 per group. FIG. 12C. TC, TG, LDL-C, HDL-C and FFA levels were detected in 6 hr fasted mice. n=6 per group. FIG. 12F. Insulin-stimulated phosphorylation of Akt in liver tissues of IgGFc or CD24Fc-treated mice. Graph shows the quantitation of pAkt relative to total Akt. n=3 per group. FIG. 12G. Representative images of H&E stained sections from the liver in the groups indicated. Arrows indicate inflammatory cell infiltration. Scale bars=100 µm. FIG. 12H. Liver weight. n=6 per group. FIG. 12L. Flow cytometry analysis of immune cell populations in eWAT. n=10 per group. FIG. 12M. mRNA levels of inflammatory genes in liver and eWAT. n=6 per group. All values are expressed as mean±SEM. *$p<0.05$, $p<0.01$, *$p<0.001$, unpaired Student's t-test (FIGS. 12B-D, H, L, M), two-way analysis of variance (ANOVA) (FIG. 12A, E, F) or Chi-square test (FIG. 12J). Data shown are representative of two independent experiments.

FIG. 13A. Representative images of H&E or Masson trichrome stained sections from the liver in the groups indicated. Scale bars=100 µm. FIG. 13B. Liver weight. FIG. 13C. Hepatic fibrosis lesion was detected in four liver lobes for each mouse. Data shown are number of lobes with or without fibrosis. FIG. 13D. mRNA levels of inflammatory genes in the liver and eWAT. All values are expressed as mean±SEM. *$p<0.05$, $p<0.01$, *$p<0.001$, unpaired Student's t-test (FIG. 13B, D), or Chi-square test (FIG. 13C). Data shown are representative of three independent experiments.

FIGS. 14A-D show CD24Fc therapy in ob/ob mice, related to FIG. 12. FIGS. 14A-D. Male ob/ob mice were treated with CD24Fc (100 µg per dose) or control IgGFc twice a week for 2 weeks. n=5 per group. FIG. 14A. Body weight. FIGS. 14B-D. Blood glucose, TC and LDL-C levels were detected in 6 hr fasted mice. All values are expressed as mean±SEM. *$p<0.05$, **$p<0.01$, unpaired Student's t-test.

FIG. 15A. Direct interaction between CD24Fc and Siglecs as determined by ELISA using recombinant proteins. Data shown are the optical density at 450 nm (OD450).

FIG. 15B. Interaction between endogenously expressed CD24 on spleen cells and recombinant Siglecs as revealed by capture ELISA. Data are shown as the optical density at 450 nm (OD450).

FIGS. 17A-F show that CD24Fc improves metabolic disorders through Siglec-E. FIGS. 17A-F. WT and Siglece$^{-/-}$ male mice were fed with HFD for 8 weeks and then administered CD24Fc (100 µg per dose) or IgGFc control twice a week for 4 more weeks and tested. n=6-8 per group. FIGS. 17A-B. TC, LDL-C, HDL-C, TG and blood glucose levels were detected in 6 hr fasted mice. FIG. 17C. GTT and ITT data. FIG. 17D. Liver weight. FIG. 17E. Representative images of H&E stained sections from liver in the groups indicated. Scale bars=100 µm. FIG. 17F. Representative images of H&E sections from eWAT in the groups indicated. Scale bars=100 µm.

FIGS. 18A-D shows that sialic acid-based pattern recognition is involved in metabolic disorders. FIGS. 18A-D. Sialic acid and sialylation levels were detected in WT mice on normal diet (ND), WT mice on high-fat diet (HFD) and ob/ob mice on normal diet. n=7-8 per group. FIGS. 18A-B. Total SA and free SA levels in serum from ND, HFD and ob/ob mice. FIGS. 18C-D. Sialylation levels on cell surface of PBMC were detected by flow cytometry, with MAL II and SNA lectins that respectively recognize either α2-3- and α2-6-linked sialic acids. All values are expressed as mean±SEM. $p<0.01$, *$p<0.001$, unpaired Student's t-test.

DETAILED DESCRIPTION

Figure 4:
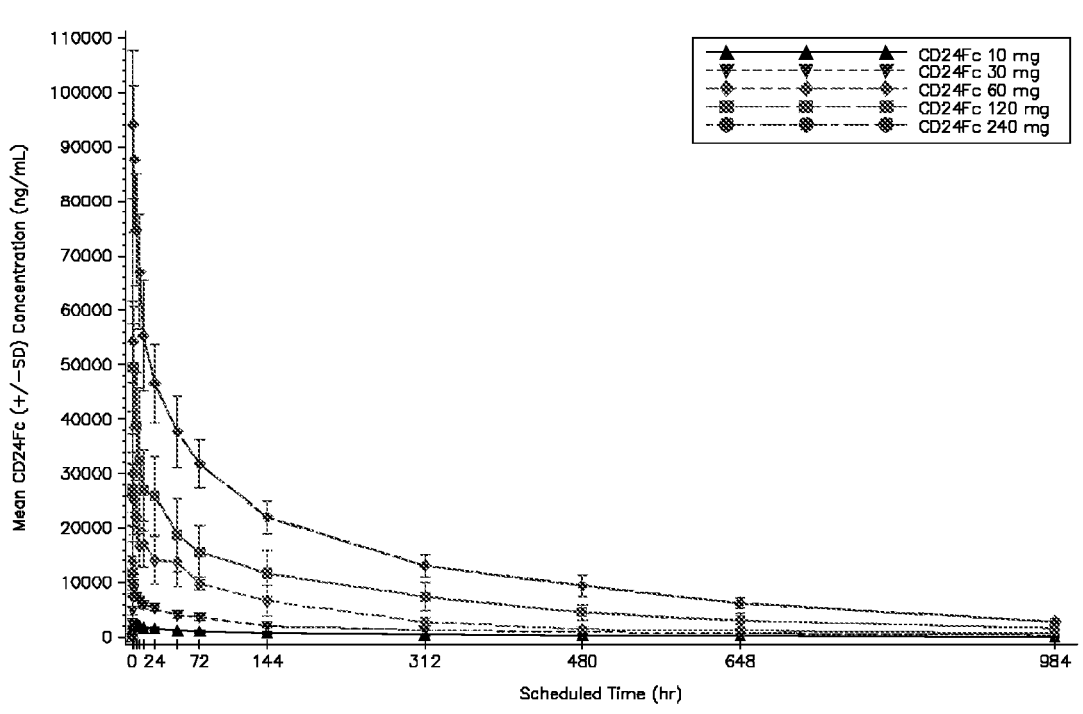
FIG. 4 shows a plot of mean plasma CD24Fc concentration ($\pm$SD) by treatment for a PK Evaluable Population in human subjects. PK=pharmacokinetic; SD=standard deviation.

The inventors have found that, surprisingly, the CD24-Siglec interactions control metabolic homeostasis. Accordingly, proteins containing a mature CD24 polypeptide effectively treat nonalcoholic steatohepatitis (NASH) and its associated morbidities such as liver lymphocyte infiltration and liver fibrosis. Although the cause of NASH is not fully understood, it is known to be associated with obesity and other metabolic disorders, such as hyperlipidemia and type II diabetes.

Initial safety of CD24Fc in healthy human subjects was initially demonstrated through a Phase I, randomized, double-blind, placebo-controlled, single ascending dose study that was conducted to assess the safety, tolerability, and PK of CD24Fc in healthy male and female adult subjects (ClinicalTrials.gov Identifier: NCT02650895). This study showed that the single dose of IV administration of CD24Fc up to 240 mg was safe and well tolerated in healthy subjects. CD24Fc has also been tested in a Phase II clinical study for the prophylaxis of acute GvHD in cancer patients undergoing allogeneic myeloablative hematopoietic stem cell transplantation (HCT). The Phase IIa portion of the trial (ClinicalTrials.gov Identifier: NCT02663622) was a randomized double blind trial comprising three single ascending dose cohorts (240 mg and 480 mg) and a single multi-dose cohort (480 mg (day −1), 240 mg (day +14) and 240 mg (day +28)) of CD24Fc in addition to SOC GVHD prophylaxis. The Phase II study has shown that IV administration of CD24Fc up to 480 mg as a single dose and in a multi-dose regimen is generally well tolerated in the intent-to-treat (ITT) population.

Using serum samples from the Phase I study in healthy subjects, a number of analytes were assayed to determine changes from baseline following CD24Fc administration. In particular, statistically-significant dose-dependent changes in serum LDL-C and leptin were observed after a single dosing of CD24Fc. Based on the data observed in the Phase I study in healthy subjects, the effects of CD24Fc on serum LDL-C and leptin, as well as other analytes related to fat metabolism continued to be studied in the Phase II GvHD prophylaxis study. Statistically significant decreases in LDL-C levels in patients receiving a single dose of 240 mg or 480 mg CD24Fc, as compared with a placebo control, have again been observed.

NASH is an important manifestation of metabolic disorders and chronic exposure of mice to a high fat diet causes moderate NASH, with hepatic steatosis, inflammation and mild fibrosis, all of which can be treated with CD24Fc. Targeted deletion of the Cd24 gene in mice exacerbated metabolic syndrome and Cd24$^{-/-}$ mice developed more severe hepatomegaly than WT controls on high fat diet. Consistently, there were more lipid droplets accumulated in the livers of Cd24$^{-/-}$ mice, and more robust liver fibrosis. In addition, of all Siglec mutations studied, only mutation of Siglece fully recapitulates the metabolic phenotype of the CD24 mutation. The essentially identical phenotypes, and the physical interaction between CD24 and Siglec E, indicate that Siglec E is the functional CD24 receptor and, consistent with this notion, CD24Fc suppresses metabolic syndrome in a Siglece-dependent mechanism.

Given the association of NASH with obesity and metabolic disorders and the ability of CD24Fc to reduce serum LDL and glucose, the involvement of the CD24 pathway in the development of NASH was studied and CD24 knockout mice were found to develop many of the symptoms of NASH. Furthermore, exogenous CD24Fc reduced steatosis, focal inflammation and liver fibrosis, all defining features of NASH, in wild type mice fed a high fat diet. Therefore, CD24Fc is valuable for treatment and/or prevention of NASH.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

A "peptide" or "polypeptide" is a linked sequence of amino acids and may be natural, synthetic, or a modification or combination of natural and synthetic.

"Substantially identical" may mean that a first and second amino acid sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, or 300 amino acids.

"Treatment" or "treating," when referring to protection of an animal from a disease, means preventing, suppressing, repressing, or completely eliminating the disease. Preventing the disease involves administering a composition of the present invention to an animal prior to onset of the disease. Suppressing the disease involves administering a composition of the present invention to an animal after induction of the disease but before its clinical appearance. Repressing the disease involves administering a composition of the present invention to an animal after clinical appearance of the disease.

A "variant" may mean a peptide or polypeptide that differs in amino acid sequence by the insertion, deletion, or conservative substitution of amino acids, but retain at least one biological activity. Representative examples of "biological activity" include the ability to bind to a toll-like receptor and to be bound by a specific antibody. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554, 101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

2. CD24

Provided herein is a CD24 protein, which may comprise the amino acid sequence of mature human CD24 or those from other mammals, which corresponds to the extracellular domain (ECD) of CD24, or a variant thereof. As described above, the sequence of the mature human CD24 protein is 31 amino acids long with a variable alanine (A) with valine (V) residue at its C-terminal end:

SETTTGTSSNSSQSTSNSGLAPNPTNATTK(V/A)
    (SEQ ID NO: 1)

The C-terminal valine or alanine may be immunogenic and may be omitted from the CD24 protein to reduce its immunogenicity. Therefore, the CD24 protein may comprise the amino acid sequence or mature human CD24 lacking the C-terminal amino acid:

SETTTGTSSNSSQSTSNSGLAPNPTNATTK (SEQ ID NO: 2)

Despite considerable sequence variations in the amino acid sequence of the mature CD24 proteins from mouse and human, they are functionally equivalent, as human CD24Fc has been shown to be active in the mouse. The amino acid sequence of the human CD24 ECD shows some sequence conservation with the mouse protein (39% identity; Gen-bank accession number NP_033976). However, it is not that surprising that the percent identity is not higher as the CD24 ECD is only 27-31 amino acids in length, depending on the species, and binding to some of its receptor(s), such as Siglec 10/G, is mediated by its sialic acid and/or galactose sugars of the glycoprotein. The amino acid sequence identity between the extracellular domains of the human Siglec-10 (GenBank accession number AF310233) and its murine homolog Siglec-G (GenBank accession number NP_766488) receptor proteins is 63%. As a result of sequence conservation between mouse and human CD24 primarily in the C-terminus and in the abundance of glyco-sylation sites, significant variations in the mature CD24 proteins may be tolerated in using the CD24 protein, espe-cially if those variations do not affect the conserved residues in the C-terminus or do not affect the glycosylation sites from either mouse or human CD24. Therefore, the CD24 protein may comprise the amino acid sequence of mature murine CD24:

NQTSVAPFPGNQNISASPNPTNATTRG (SEQ ID NO: 3).

The amino acid sequence of the human CD24 ECD shows more sequence conservation with the cynomolgus monkey protein (52% identity; UniProt accession number UniPro-tKB-I7GKK1) than with mouse. Again, this is not surprising given that the percent identity is not higher as the ECD is only 29-31 amino acids in length in these species, and the role of sugar residues in binding to its receptor(s). The amino acid sequence of cynomolgous Siglec-10 receptor has not been determined but the amino acid sequence identity between the human and rhesus monkey Siglec-10 (GenBank accession number XP_001116352) proteins is 89%. There-fore, the CD24 protein may also comprise the amino acid sequence of mature cynomolgous (or rhesus) monkey CD24:

TVTTSAPLSSNSPQNTSTTPNPANTTTKA (SEQ ID NO: 10)

The CD24 protein may be soluble. The CD24 protein may further comprise an N-terminal signal peptide, to allow secretion from a cell expressing the protein. The signal peptide sequence may comprise the amino acid sequence MGRAMVARLGLGLLLLALLLPTQIYS (SEQ ID NO: 4). Alternatively, the signal sequence may be any of those that are found on other transmembrane or secreted proteins, or those modified from the existing signal peptides known in the art.

a. Fusion

The CD24 protein may be fused at its N- or C-terminal end to a protein tag, which may comprise a portion of a mammalian Ig protein, which may be human or mouse or another species. The portion may comprise an Fc region of the Ig protein. The Fc region may comprise at least one of the hinge region, CH2, CH3, and CH4 domains of the Ig protein. The Ig protein may be human IgG1, IgG2, IgG3, IgG4, or IgA, and the Fc region may comprise the hinge region, and CH2 and CH3 domains of the Ig. The Fc region may comprise the human immunoglobulin G1 (IgG1) iso-type SEQ ID NO: 7. The Ig protein may also be IgM, and the Fc region may comprise the hinge region and CH2, CH3, and CH4 domains of IgM. The protein tag may be an affinity tag that aids in the purification of the protein, and/or a solubility-enhancing tag that enhances the solubility and recovery of functional proteins. The protein tag may also increase the valency of the CD24 protein. The protein tag may also comprise GST, His, FLAG, Myc, MBP, NusA, thioredoxin (TRX), small ubiquitin-like modifier (SUMO), ubiquitin (Ub), albumin, or a Camelid Ig. Methods for making fusion proteins and purifying fusion proteins are well known in the art.

Based on preclinical research, for the construction of the fusion protein CD24Fc identified in the examples, the trun-cated form of native CD24 molecule of 30 amino acids, which lacks the final polymorphic amino acid before the GPI signal cleavage site (that is, a mature CD24 protein having SEQ ID NO: 2), has been used. The mature human CD24 sequence is fused to a human IgG1 Fc domain (SEQ ID NO: 7). The full length CD24Fc fusion protein is provided in SEQ ID NO: 5 (FIG. 1), and the processed version of CD24Fc fusion protein that is secreted from the cell (i.e. lacking the signal sequence which is cleaved off) is provided in SEQ ID NO: 6. Processed polymorphic variants of mature CD24 (that is, mature CD24 protein having SEQ ID NO: 1) fused to IgG1 Fc may comprise SEQ ID NO: 11 or 12.

b. Production

The CD24 protein may be heavily glycosylated, and may be involved in functions of CD24 such as costimulation of immune cells and interaction with a damage-associated molecular pattern molecule (DAMP). The CD24 protein may be prepared using a eukaryotic expression system. The expression system may entail expression from a vector in mammalian cells, such as Chinese Hamster Ovary (CHO) cells. The system may also be a viral vector, such as a replication-defective retroviral vector that may be used to infect eukaryotic cells. The CD24 protein may also be produced from a stable cell line that expresses the CD24 protein from a vector or a portion of a vector that has been integrated into the cellular genome. The stable cell line may express the CD24 protein from an integrated replication-defective retroviral vector. The expression system may be GPEx™.

c. Pharmaceutical composition

The CD24 protein may be contained in a pharmaceutical composition, which may comprise a pharmaceutically acceptable amount of the CD24 protein. The pharmaceutical composition may comprise a pharmaceutically acceptable carrier. The pharmaceutical composition may comprise a solvent, which may keep the CD24 protein stable over an extended period. The solvent may be PBS, which may keep the CD24 protein stable for at least 66 months at −20° C. (−15-25° C.). The solvent may be capable of accommodat-ing the CD24 protein in combination with another drug.

The pharmaceutical composition may be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be pro-vided in a powder form for reconstitution with a suitable vehicle including, but not limited to, sterile, pyrogen-free water.

The pharmaceutical composition may also be formulated as a depot preparation, which may be administered by implantation or by intramuscular injection. The composition may be formulated with suitable polymeric or hydrophobic materials (as an emulsion in an acceptable oil, for example), ion exchange resins, or as sparingly soluble derivatives (as a sparingly soluble salt, for example).

d. Dosage

The dose of the CD24 protein may ultimately be determined through a clinical trial to determine a dose with acceptable toxicity and clinical efficacy. The initial clinical dose may be estimated through pharmacokinetics and toxicity studies in rodents and non-human primates. The dose of the CD24 protein may be 0.01 mg/kg to 1000 mg/kg, and may be 1 to 500 mg/kg, depending on the desired amount of LDL-C-lowering and the route of administration. The CD24 protein may be administered by intravenous infusion or subcutaneous or intramural [that is, within the wall of a cavity or organ] injection, and the dose may be 10-1000 mg, 10-500 mg, 10-480 mg, 10-120 mg, or 10, 30, 60, 120, 240 mg or 480 mg, where the subject is a human.

3. Siglec Agonists

Provided herein are agonists of Siglecs (Sialic acid-binding immunoglobulin-type lectins). Siglecs are a diverse family of cell surface proteins that bind sialic acid containing structures such as glycoproteins like CD24. Accordingly, Siglecs may have a number of different ligands and a particular sialic-acid containing ligand may bind more than one Siglec receptor. In one embodiment the Siglec agonist binds to a Siglec containing an ITIM (Immunoreceptor tyrosine-based inhibitory motif) in its cytosolic region. In another embodiment the agonist binds to a member of the human CD33-related Siglec family. In a preferred embodiment, the agonist binds to at least one of human Siglec-3, Siglec-5, Siglec-6, Siglec-7, Siglec-8, Siglec-9, Siglec-10, Siglec-11, and Siglec-12.

The Siglec agonist can be a natural Siglec ligand, such as CD24, or a portion thereof as described herein. In another embodiment, the Siglec agonist is a sialic acid-containing structure such as a glycoprotein, a glycolipid, or other sialic acid-containing structure. In yet another embodiment the Siglec agonist is an antibody that binds to the Siglec and triggers the endogenous intracellular signaling pathway mediated by the Siglec receptor.

The Siglec agonist may activate ITIM-containing Siglecs by co-inducing tyrosine phosphorylation of the ITIM domain, which results in recruitment of SHP-1 and/or SHP-2 phosphatases to Siglec or another ITIM-containing structure.

4. Methods of Treatment

Provided herein are methods of treating or preventing non-alcoholic fatty liver disease (NAFLD) in a subject, including NASH in particular, or the symptoms associated with NASH.

Such symptoms may include steatosis, focal inflammation and liver fibrosis. The CD24 protein or Siglec agonist described herein may be administered to the subject. The subject may be a mammal such as a human.

a. Administration

The route of administration of the pharmaceutical composition may be parenteral. Parenteral administration includes, but is not limited to, intravenous, intraarterial, intraperitoneal, subcutaneous, intramuscular, intrathecal, intraarticular, and direct injection. The pharmaceutical composition may be administered to a human patient, cat, dog, large animal, or an avian. The composition may be administered 1, 2, 3, 4, 5, 6, 7, 8, 9, 10, 11, or 12 times per day.

b. Combination Treatment

The CD24 protein or Siglec agonist may be combined with another treatment, which may be another drug such as a lipid-altering agent, GLP-1 receptor agonist, PPAR agonist, or Obeticholic acid. The CD24 protein or Siglec agonist and the other drug may be administered together or sequentially.

The CD24 protein or Siglec agonist may be administered simultaneously or metronomically with other treatments. The term "simultaneous" or "simultaneously" as used herein, means that the CD24 protein or Siglec agonist and other treatment be administered within 48 hours, preferably 24 hours, more preferably 12 hours, yet more preferably 6 hours, and most preferably 3 hours or less, of each other. The term "metronomically" as used herein means the administration of the agent at times different from the other treatment and at a certain frequency relative to repeat administration.

The CD24 protein or Siglec agonist may be administered at any point prior to another treatment including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins, 50 mins, 45 mins, 40 mins, 35 mins, 30 mins, 25 mins, 20 mins, 15 mins, 10 mins, 9 mins, 8 mins, 7 mins, 6 mins, 5 mins, 4 mins, 3 mins, 2 mins, and 1 mins. The CD24 protein or Siglec agonist may be administered at any point prior to a second treatment of the CD24 protein or Siglec agonist including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins, 50 mins, 45 mins, 40 mins, 35 mins, 30 mins, 25 mins, 20 mins, 15 mins, 10 mins, 9 mins, 8 mins, 7 mins, 6 mins, 5 mins, 4 mins, 3 mins, 2 mins, and 1 mins.

The CD24 protein or Siglec agonist may be administered at any point after another treatment including about 1 min, 2 mins, 3 mins, 4 mins, 5 mins, 6 mins, 7 mins, 8 mins, 9 mins, 10 mins, 15 mins, 20 mins, 25 mins, 30 mins, 35 mins, 40 mins, 45 mins, 50 mins, 55 mins, 1 hr, 2 hr, 3 hr, 4 hr, 6 hr, 8 hr, 10 hr, 12 hr, 14 hr, 16 hr, 18 hr, 20 hr, 22 hr, 24 hr, 26 hr, 28 hr, 30 hr, 32 hr, 34 hr, 36 hr, 38 hr, 40 hr, 42 hr, 44 hr, 46 hr, 48 hr, 50 hr, 52 hr, 54 hr, 56 hr, 58 hr, 60 hr, 62 hr, 64 hr, 66 hr, 68 hr, 70 hr, 72 hr, 74 hr, 76 hr, 78 hr, 80 hr, 82 hr, 84 hr, 86 hr, 88 hr, 90 hr, 92 hr, 94 hr, 96 hr, 98 hr, 100 hr, 102 hr, 104 hr, 106 hr, 108 hr, 110 hr, 112 hr, 114 hr, 116 hr, 118 hr, and 120 hr. The CD24 protein or Siglec agonist may be administered at any point prior after a previous CD24/Siglec agonist treatment including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins, 50 mins, 45 mins, 40 mins, 35 mins, 30 mins, 25 mins, 20 mins, 15 mins, 10 mins, 9 mins, 8 mins, 7 mins, 6 mins, 5 mins, 4 mins, 3 mins, 2 mins, and 1 mins.

Example 1

Soluble CD24 Proteins

FIG. 1. shows the amino acid composition of the CD24Fc fusion protein, in which the sequence of mature extracellular domain of human CD24 was fused to human IgG1 Fc. FIG. 2 shows amino acid sequence variations between mature CD24 proteins from mouse (SEQ ID NO: 3) and human (SEQ ID NO: 2). The potential O-glycosylation sites are bolded, and the N-glycosylation sites are underlined.

Example 2

CD24 Pharmacokinetics in Mice 1 mg of CD24Fc (CD24Fc) was injected into naïve C57BL/6 mice and collected blood samples at different timepoints (5 min, 1 hr, 4 hrs, 24 hrs, 48 hrs, 7 days, 14 days and 21 days) with 3 mice in each timepoint. The sera were diluted 1:100 and the levels of CD24Fc was detected using a sandwich ELISA using purified anti-human CD24 (3.3 µg/ml) as the capturing antibody and peroxidase conjugated goat anti-human IgG Fc (5 µg/ml) as the detecting antibodies. As shown in FIG. 3A, the decay curve of CD24Fc revealed a typical biphase decay of the protein. The first biodistribution phase had a half-life of 12.4 hours. The second phase follows a model of first-order elimination from the central compartment. The half-life for the second phase was 9.54 days, which is similar to that of antibodies in vivo.

These data suggest that the fusion protein is very stable in the blood stream. In another study in which the fusion protein was injected subcutaneously, an almost identical half-life of 9.52 days was observed (FIG. 3B). More importantly, while it took approximately 48 hours for the CD24Fc to reach peak levels in the blood, the total amount of the fusion protein in the blood, as measured by AUC, was substantially the same by either route of injection (FIG. 3C). Thus, from therapeutic point of view, different route of injection should not affect the therapeutic effect of the drug. This observation greatly simplified the experimental design for primate toxicity and clinical trials.

Example 3

CD24 Pharmacokinetics in Humans

This example shows an analysis of the pharmacokinetics of a CD24 protein in humans based on a clinical study which is described in more detail below (see the Methods section of this example).

Plasma CD24Fc Concentration

As shown in FIG. 4, the mean plasma concentration of CD24Fc increased proportionally to the dose of CD24Fc administered. For all dose groups except 120 mg, the maximum mean plasma concentration of CD24Fc was reached at 1 hour post-dose. The maximum mean plasma concentration of CD24Fc for the 120 mg group was reached at 2 hours post-dose. By Day 42 (984 hours), the mean plasma concentration of CD24Fc for all groups had decreased to between 2% and 4% of the maximum mean plasma concentration.

Table 1 summarizes the plasma CD24Fc PK parameters by treatment for the PK Evaluable Population.

TABLE 1

| Summary of Plasma CD24Fc Pharmacokinetic Parameters by Treatment-PK Evaluable Population | | | | | |
|---|---|---|---|---|---|
| Parameter Statistic | CD24Fc 10 mg (N = 6) | CD24Fc 30 mg (N = 6) | CD24Fc 60 mg (N = 6) | CD24Fc 120 mg (N = 6) | CD24Fc 240 mg (N = 6) |
| $C_{max}$ (ng/mL) | | | | | |
| n | 6 | 6 | 6 | 6 | 6 |
| Mean (SD) | 2495 (576) | 9735 (1715) | 30 083 (7179) | 52 435 (9910) | 95 865 (10 734) |
| CV % | 23.1 | 17.6 | 23.9 | 18.9 | 11.2 |
| Median | 2371 | 9218 | 29 026 | 50 401 | 93 206 |
| Min, Max | 1,967, 3,390 | 8,583, 13,086 | 22,557, 42,628 | 40,434, 65,704 | 81,296, 110,110 |
| Geometric mean | 2,442 | 9,625 | 29,424 | 51,666 | 95,365 |
| Geometric CV % | 22.8 | 16.1 | 23.0 | 19.0 | 11.2 |
| $AUC_{0\text{-}42\,d}$ (ng*hr/mL) | | | | | |
| n | 6 | 6 | 6 | 6 | 6 |
| Mean (SD) | 423,061 (99,615) | 1,282,430 (88,798) | 3,226,255 (702,862) | 6,541,501 (2,190,944) | 12,704,705 (1,918,596) |
| CV % | 23.5 | 6.9 | 21.8 | 33.5 | 15.1 |
| Median | 434,043 | 1,302,719 | 3,124,933 | 5,785,142 | 12,563,426 |
| Min, Max | 291,020, 528,079 | 1,175,733, 1,403,024 | 2,487,550, 4,139,748 | 4,485,193, 9,415,266 | 10,466,635, 15,693,606 |
| Geometric mean | 412,795 | 1,279,851 | 3,163,252 | 6,249,552 | 12,586,731 |
| Geometric CV % | 25.0 | 7.0 | 22.0 | 33.8 | 15.0 |
| $AUC_{0\text{-}inf}$ (ng*hr/mL) | | | | | |
| n | 6 | 6 | 6 | 6 | 6 |
| Mean (SD) | 462,260 (116,040) | 1,434,464 (131,316) | 3,497,196 (705,653) | 7,198,196 (2,458,320) | 13,861,796 (1,962,780) |
| CV % | 25.1 | 9.2 | 20.2 | 34.2 | 14.2 |
| Median | 470,426 | 1,422,205 | 3,519,732 | 6,463,665 | 13,713,034 |
| Min, Max | 310,956, 596,599 | 1,281,715, 1,650,503 | 2,703,655, 4,309,023 | 4,910,640, 10,479,940 | 11,822,988, 17,175,236 |
| Geometric mean | 449,583 | 1,429,578 | 3,437,036 | 6,862,129 | 13,750,972 |
| Geometric CV % | 26.7 | 9.0 | 20.7 | 34.6 | 13.8 |

TABLE 1-continued

Summary of Plasma CD24Fc Pharmacokinetic Parameters by Treatment-PK Evaluable Population

| Parameter Statistic | CD24Fc 10 mg (N = 6) | CD24Fc 30 mg (N = 6) | CD24Fc 60 mg (N = 6) | CD24Fc 120 mg (N = 6) | CD24Fc 240 mg (N = 6) |
|---|---|---|---|---|---|
| $T_{max}$ (hr) | | | | | |
| n | 6 | 6 | 6 | 6 | 6 |
| Mean (SD) | 1.15 (0.42) | 1.17 (0.41) | 1.01 (0.01) | 1.34 (0.51) | 1.33 (0.52) |
| CV % | 36.1 | 35.0 | 1.2 | 38.0 | 38.7 |
| Median | 1.00 | 1.00 | 1.00 | 1.03 | 1.00 |
| Min, Max | 0.92, 2.00 | 1.00, 2.00 | 1.00, 1.03 | 1.00, 2.00 | 1.00, 2.00 |
| $t^{1/2}$ (hr) | | | | | |
| n | 6 | 6 | 6 | 6 | 6 |
| Mean (SD) | 280.83 (22.37) | 327.10 (41.32) | 279.82 (65.59) | 286.45 (23.38) | 285.33 (24.33) |
| CV % | 8.0 | 12.6 | 23.4 | 8.2 | 8.5 |
| Median | 279.61 | 317.23 | 264.69 | 290.76 | 287.74 |
| Min, Max | 258.87, 321.26 | 289.82, 394.24 | 210.18, 362.46 | 243.89, 309.26 | 249.24, 322.26 |
| AUCextr (%) | | | | | |
| n | 6 | 6 | 6 | 6 | 6 |
| Mean (SD) | 7.61 (2.14) | 10.44 (2.94) | 7.88 (4.26) | 8.92 (1.94) | 8.46 (1.99) |
| CV % | 28.1 | 28.2 | 54.0 | 21.8 | 23.5 |
| Median | 7.16 | 10.01 | 6.35 | 9.27 | 8.45 |
| Min, Max | 5.46, 11.47 | 7.10, 15.05 | 3.92, 14.48 | 5.49, 10.99 | 5.56, 11.50 |
| CL (L/hr) | | | | | |
| n | 6 | 6 | 6 | 6 | 6 |
| Mean (SD) | 0.0229 (0.0061) | 0.0211 (0.0019) | 0.0178 (0.0036) | 0.0183 (0.0058) | 0.0176 (0.0023) |
| CV % | 26.7 | 8.8 | 20.5 | 31.7 | 13.3 |
| Median | 0.0216 | 0.0211 | 0.0173 | 0.0191 | 0.0175 |
| Min, Max | 0.0168, 0.0322 | 0.0182, 0.0234 | 0.0139, 0.0222 | 0.0115, 0.0244 | 0.0140, 0.0203 |
| Vd (L) | | | | | |
| n | 6 | 6 | 6 | 6 | 6 |
| Mean (SD) | 9.153 (1.943) | 9.867 (0.804) | 7.289 (2.592) | 7.491 (2.202) | 7.276 (1.426) |
| CV % | 21.2 | 8.1 | 35.6 | 29.4 | 19.6 |
| Median | 8.507 | 10.007 | 7.486 | 7.691 | 7.151 |
| Min, Max | 7.326, 12.010 | 8.771, 10.958 | 4.222, 11.139 | 4.933, 9.974 | 5.814, 9.438 |

$AUC_{0-42\ d}$ = area under the concentration-time curve from time 0 to 42 days;

$AUC_{0-inf}$ = area under the concentration-time curve extrapolated from time 0 to infinity;

AUCextr = percentage of $AUC_{0-inf}$ that was due to extrapolation from the time of the last measurable concentration, per subject, to infinity;

CL = total body clearance;

$C_{max}$ = maximum observed plasma drug concentration;

CV % = coefficient of variation;

Min = minimum;

Max = maximum;

SD = standard deviation;

$t^{1/2}1/2$ = terminal elimination half-life;

$T_{max}$ = time of maximum observed plasma drug concentration;

$V_d$ = volume of distribution.

Plasma CD24Fc Dose Proportionality Analysis

Figure 5:
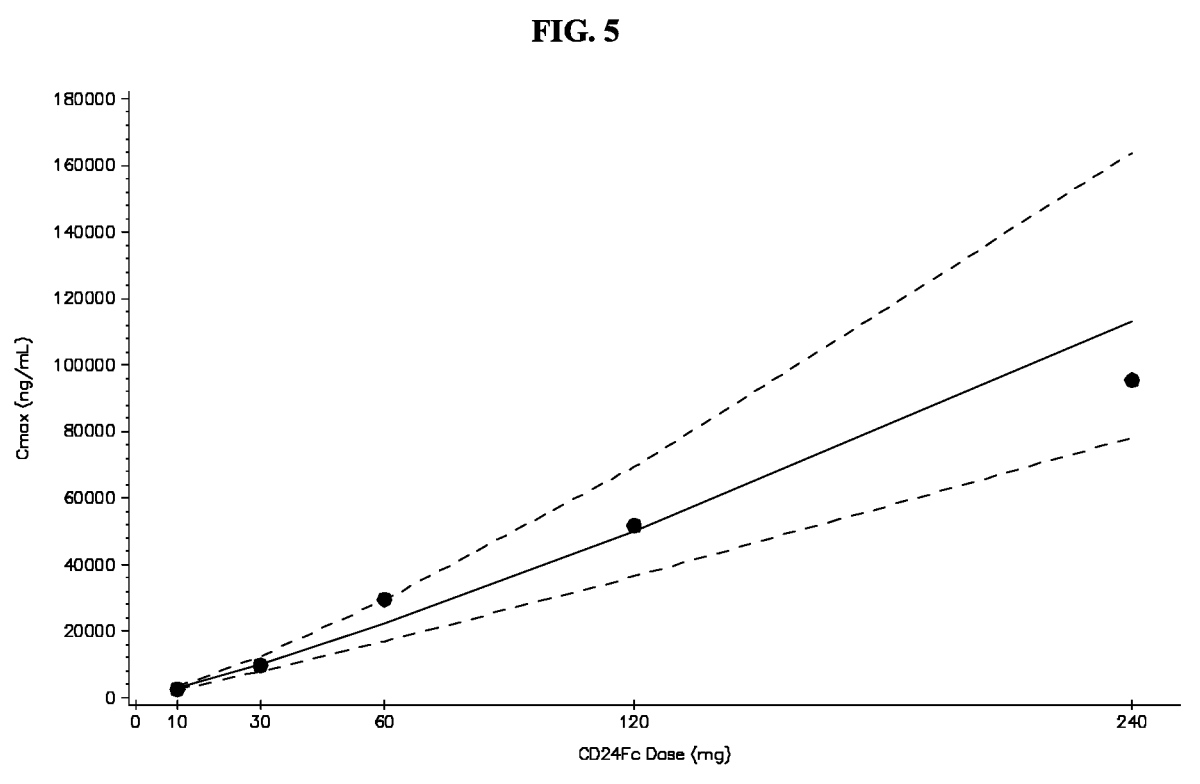
Figure 6:
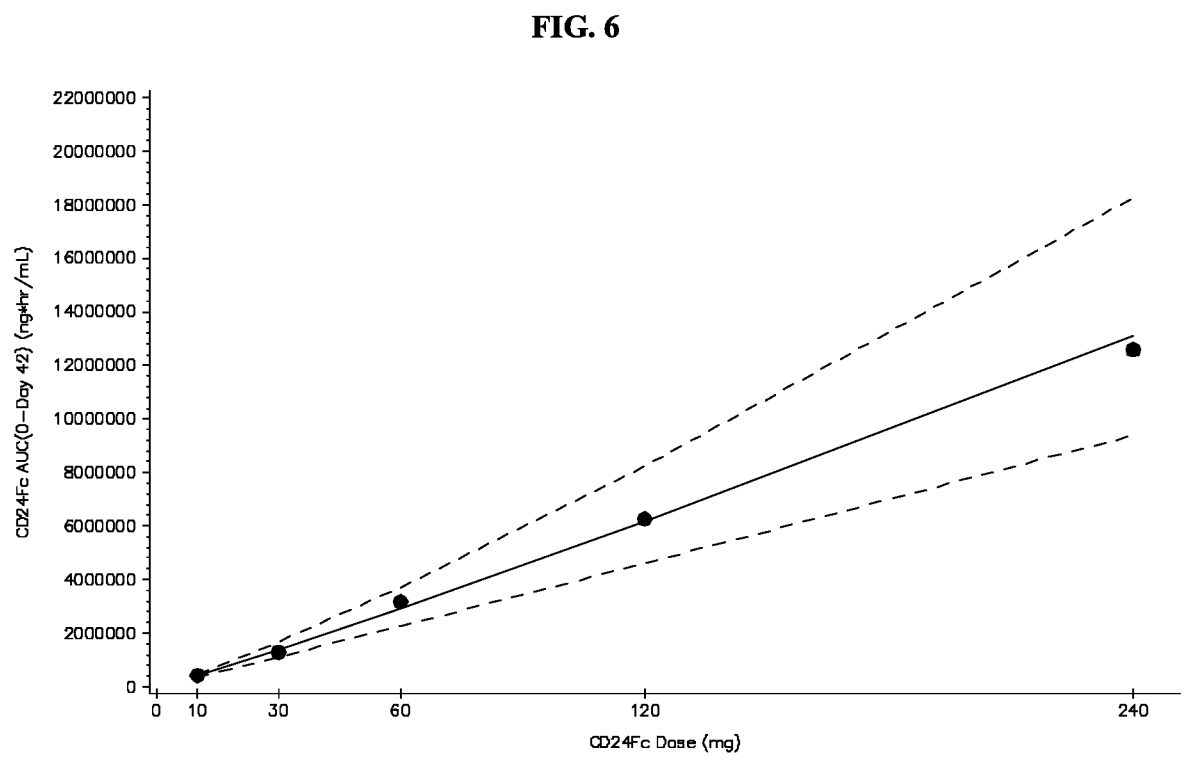
Figure 7:
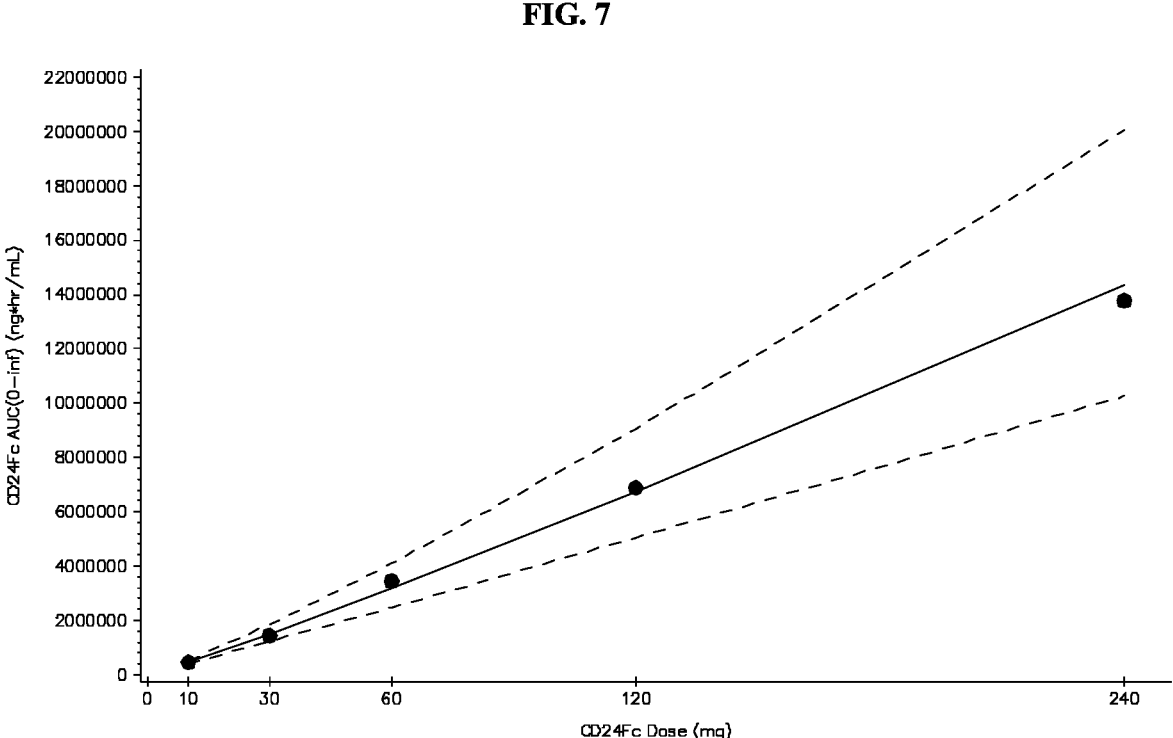
FIG. 7 shows a dose proportionality plot of CD24Fc $AUC_{0-inf}$ versus dose for a PK Evaluable Population.

FIG. 5 shows a dose proportionality plot of CD24Fc $C_{max}$ versus dose for the PK Evaluable Population. FIG. 6 shows a dose proportionality plot of CD24Fc $AUC_{0-42d}$ versus dose for the PK Evaluable Population. FIG. 7 shows a dose proportionality plot of CD24Fc $AUC_{0-inf}$ versus dose for the PK Evaluable Population. Table 2 shows a power analysis of dose proportionality.

TABLE 2

Power Analysis of Dose Proportionality: Plasma CD24Fc Pharmacokinetic Parameters - PK Evaluable Population

| Parameter Statistic | CD24Fc 10 mg (N = 6) | CD24Fc 30 mg (N = 6) | CD24Fc 60 mg (N = 6) | CD24Fc 120 mg (N = 6) | CD24Fc 240 mg (N = 6) | Dose Proportionality Slope Estimate | Standard Error | 90% CI |
|---|---|---|---|---|---|---|---|---|
| $C_{max}$(ng/mL) | | | | | | 1.172 | 0.040 | (1.105, 1.240) |
| Geometric mean | 2,441.8 | 9,624.9 | 29,424.4 | 51,666.4 | 95,364.9 | | | |
| Geometric CV % | 22.8 | 16.1 | 23.0 | 19.0 | 11.2 | | | |
| $AUC_{0-42\ d}$ (ng* hr/mL) | | | | | | 1.088 | 0.036 | (1.027, 1.148) |

TABLE 2-continued

| | | | Power Analysis of Dose Proportionality: Plasma CD24Fc Pharmacokinetic Parameters - PK Evaluable Population | | | | | |
|---|---|---|---|---|---|---|---|---|
| | CD24Fc | CD24Fc | CD24Fc | CD24Fc | CD24Fc | Dose Proportionality | | |
| Parameter Statistic | 10 mg (N = 6) | 30 mg (N = 6) | 60 mg (N = 6) | 120 mg (N = 6) | 240 mg (N = 6) | Slope Estimate | Standard Error | 90% CI |
| Geometric mean | 412,794.8 | 1,279,850.8 | 3,163,251.7 | 6,249,551.9 | 12,586,731.3 | | | |
| Geometric CV % | 25.0 | 7.0 | 22.0 | 33.8 | 15.0 | | | |
| $AUC_{0\text{-}inf}$ (ng* hr/mL) | | | | | | 1.087 | 0.036 | (1.026, 1.148) |
| Geometric mean | 449,583.5 | 1,429,577.5 | 3,437,035.6 | 6,862,128.7 | 13,750,972.4 | | | |
| Geometric CV % | 26.7 | 9.0 | 20.7 | 34.6 | 13.8 | | | |

Geometric CV% = 100*sqrt (exp($SD^2$)−1), where SD was the standard deviation of the log-transformed data. The power model was fitted by restricted maximum likelihood, regressing the log-transformed PK parameter on log transformed dose. Both the intercept and slope were fitted as fixed effects. Dose proportionality was not rejected if the 90% CI lies within (0.8, 1.25).
$AUC_{0\text{-}42\ d}$ = area under the concentration-time curve from time 0 to 42 days;
$AUC_{0\text{-}inf}$ = area under the concentration-time curve extrapolated from time 0 to infinity;
CI = confidence interval;
$C_{max}$ = maximum observed plasma drug concentration;
CV % = coefficient of variation; PK = pharmacokinetic;
SD = standard deviation.

The $C_{max}$ slope estimate was 1.172 with a 90% CI of 1.105 to 1.240. The $AUC_{0\text{-}42d}$ slope estimate was 1.088 with a 90% CI of 1.027 to 1.148. The $AUC_{0\text{-}inf}$ slope estimate was 1.087 with a 90% CI of 1.026 to 1.1.

Pharmacokinetic Conclusions

The $C_{max}$ and AUCs of plasma CD24Fc increased proportionally to the doses administered in mouse, monkey and human. The plasma CD24Fc reached $T_{max}$ between 1.01 and 1.34 hours. The $t_{1/2}$ of plasma CD24Fc ranged between 280.83 and 327.10 hours.

Methods

This was a Phase I, randomized, double-blind, placebo-controlled, single ascending dose study to assess the safety, tolerability, and pharmacokinetics of CD24Fc in healthy male and female adult subjects (ClinicalTrials.gov Identifier: NCT02650895). A total of 40 subjects in 5 cohorts of 8 subjects each were enrolled in this study. Six of the 8 subjects in each cohort received study drug and 2 subjects received placebo (0.9% sodium chloride, saline). The first cohort was dosed with 10 mg. Succeeding cohorts received 30 mg, 60 mg, 120 mg, and 240 mg of CD24Fc or matching placebo and were dosed at least 3 weeks apart to allow for review of safety and tolerability data for each prior cohort. Administration of the next higher dose to a new cohort of subjects was permitted only if adequate safety and tolerability had been demonstrated.

In each cohort, the initial 2 subjects were 1 study drug recipient and 1 placebo recipient on Day 1. The 3rd to 5th and 6th to 8th subjects were dosed after Day 7 (a minimum of 24 hours apart between the subgroups). Each subject was dosed at least 1 hour apart in the same subgroup. If necessary, dosing of the rest of subjects was delayed pending review of any significant safety issues that may have arisen during the post-dose period involving the first or second subgroups in that cohort. The subsequent cohort was dosed at least 3 weeks after the prior cohort.

Screening Period:

The Screening Visit (Visit 1) occurred up to 21 days prior to the beginning of the active treatment period. After providing informed consent, subjects underwent screening procedures for eligibility.

Treatment Period:

Subjects were admitted to the Clinical Pharmacology Unit (CPU) on Day −1 (Visit 2), and the randomized treatment period began on Day 1 following a 10-hour minimum overnight fast. Subjects were randomly assigned to treatment with CD24Fc or placebo as a single dose. Subjects remained confined until the morning of Day 4.

Follow-Up:

All subjects returned to the CPU on Day 7, Day 14, Day 21, Day 28, and Day 42 (±1 day) for follow-up visits (Visit 3, Visit 4, Visit 5, Visit 6, and Visit 7). Visit 7 was the final visit for all subjects.

Duration of Treatment: The total study duration for each subject was up to 63 days. Single-dose administration occurred on Day 1.

Number of Subjects:

Planned: 40 subjects
Screened: 224 subjects
Randomized: 40 subjects
Completed: 39 subjects
Discontinued: 1 subject Diagnosis and Main Criteria for Inclusion: The population for this study was healthy males and females between the ages of 18 and 55 years, inclusive, with a body mass index between 18 kg/m² and 30 kg/m², inclusive.

Investigational Product and Comparator Information:

CD24Fc: single dose of 10 mg, 30 mg, 60 mg, 120 mg, or 240 mg administered via IV infusion; lot number: 09MM-036. CD24Fc was a fully humanized fusion protein consisting of the mature sequence of human CD24 and the fragment crystallizable region of human immunoglobulin G1 (IgG1Fc). CD24Fc was supplied as a sterile, clear, colorless, preservative-free, aqueous solution for IV administration. CD24Fc was formulated as single dose injection solution, at a concentration of 10 mg/mL and a pH of 7.2. Each CD24Fc vial contained 160 mg of CD24Fc, 5.3 mg of sodium chloride, 32.6 mg of sodium phosphate dibasic heptahydrate, and 140 mg of sodium phosphate monobasic monohydrate in 16 mL±0.2 mL of CD24Fc. CD24Fc was supplied in clear borosilicate glass vials with chlorobutyl rubber stoppers and aluminum flip-off seals.

Matching placebo (0.9% sodium chloride, saline) administered via IV infusion; lot numbers: P296855, P311852, P300715, P315952.

The intent-to-treat (ITT) Population consisted of all subjects who received at least 1 dose of the study drug. The ITT Population was the primary analysis population for subject information and safety evaluation.

Clinical laboratory evaluations (chemistry, hematology, and urinalysis) were summarized by treatment and visit. Change from baseline was also summarized. Vital signs (blood pressure, heart rate, respiratory rate, and temperature) were summarized by treatment and time point. Change from baseline was also summarized. All physical examination data were listed. Electrocardiogram parameters and the change from baseline were summarized. Serum metabolic parameters were detected at pre-dosing baseline, and at 7, 14 and 42 days after dosing. PBMC samples were collected from human subjects on Day −1 (pre-treatment) and Day 3 (post-treatment) for RNA-sequencing. In particular, fasting LDL-C and high density lipoprotein cholesterol were obtained on Day −1, Day 7, and Day 42 for Cohort 1 (CD24Fc 10 mg group). Beginning with Cohort 2 (Cd24Fc 30 mg group), this lipid sampling was expanded to include Day 14.

Example 4

CD24 Lowers LDL-C Levels

Figure 8:
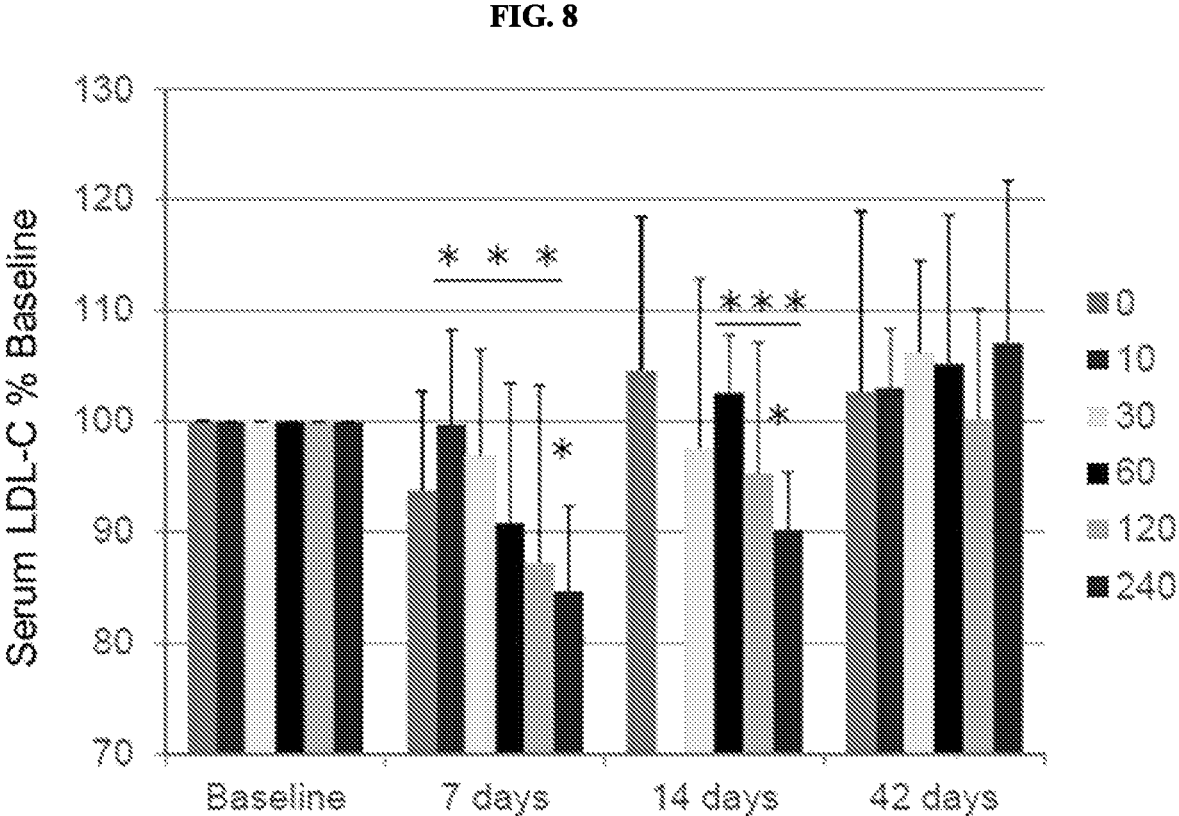
FIG. 8 shows CD24Fc Decreased Human Serum LDL-C in Healthy Subjects. Serum samples were taken from Subjects in the Phase I trial involving subjects receiving single CD24Fc doses: 0, 10, 30, 60, 120, 240 mg. The level of LDL-C measured at pre-dosing baseline, and 7, 14 or 42 days after dosing. Based on linear regression analysis, dose-dependent reduction of LDL-C was observed on days 7 and 14 among patients receiving 30-240 mg of CD24Fc (***P<0.0001). When compared with placebo control, 240 mg of CD24Fc significantly reduced LDL-C at days 7 and 14 (*, P<0.05).

This example demonstrates that CD24 lowers LDL-C and increases leptin. Changes of fasting LDL-C in plasma from baseline were analyzed in a clinical study which is described in Example 3. Fasting LDL-C levels were determined among samples obtained on Day −1, Day 7, and Day 42 for Cohort 1 (CD24Fc 10 mg group). Beginning with Cohort 2 (CD24Fc 30 mg group), this lipid sampling was expanded to include Day 14. The data are summarized in Table 3. Due to an incomplete dataset in Cohort 1, Cohorts 2-5 were used to analyze for dose-dependent reduction of LDL-C levels. A statistically significant dose-dependent reduction was observed as shown in Table 3 and FIG. 8. In particular, when compared with placebo control, a significant reduction of LDL-C was observed in subjects receiving 240 mg of CD24Fc on days 7 and 14.

TABLE 3

Change in LDL-C levels on Day 7 (U1), Day 14 (U2) and Day 42 (U3) from baseline (U0, defined as 100%)

| Dose | Obs | Variable | Label | N | Mean | Std Dev | Minimum | Maximum |
|---|---|---|---|---|---|---|---|---|
| 10 mg | 6 | u0 | Baseline LDL | 6 | 100.0000000 | 0 | 100.0000000 | 100.0000000 |
| | | u1 | 7 days LDL ratio | 5 | 99.6785886 | 8.5665505 | 87.0370370 | 107.7586207 |
| | | u2 | 14 days LDL ratio | 0 | — | — | — | — |
| | | u3 | 42 days LDL ratio | 6 | 102.9957054 | 5.3134796 | 96.8085106 | 110.5769231 |
| 30 mg | 6 | u0 | Baseline LDL | 6 | 100.0000000 | 0 | 100.0000000 | 100.0000000 |
| | | u1 | 7 days LDL ratio | 6 | 96.9190313 | 9.5257894 | 86.9047619 | 113.4328358 |
| | | u2 | 14 days LDL ratio | 6 | 97.5816504 | 15.2482354 | 84.5238095 | 122.3880597 |
| | | u3 | 42 days LDL ratio | 6 | 106.1959745 | 8.2383407 | 95.2830189 | 113.4328358 |
| 60 mg | 6 | u0 | Baseline LDL | 6 | 100.0000000 | 0 | 100.0000000 | 100.0000000 |
| | | u1 | 7 days LDL ratio | 6 | 90.7620588 | 12.6697467 | 72.0720721 | 106.1728395 |
| | | u2 | 14 days LDL ratio | 6 | 102.5671170 | 5.2461286 | 96.5517241 | 110.3773585 |
| | | u3 | 42 days LDL ratio | 6 | 105.1546943 | 13.4340830 | 93.2773109 | 127.1604938 |
| 120 mg | 6 | u0 | Baseline LDL | 6 | 100.0000000 | 0 | 100.0000000 | 100.0000000 |
| | | u1 | 7 days LDL ratio | 6 | 87.1476632 | 16.0595374 | 61.7391304 | 106.4516129 |
| | | u2 | 14 days LDL ratio | 6 | 95.2625418 | 11.8341667 | 83.4782609 | 116.1290323 |
| | | u3 | 42 days LDL ratio | 6 | 100.1377165 | 9.9404474 | 87.1794872 | 112.3456790 |
| 240 mg | 6 | u0 | Baseline LDL | 6 | 100.0000000 | 0 | 100.0000000 | 100.0000000 |
| | | u1* | 7 days LDL ratio | 6 | 84.6472221 | 7.6553896 | 71.5596330 | 94.0476190 |
| | | u2* | 14 days LDL ratio | 5 | 90.1393086 | 5.2501807 | 86.2385321 | 99.0825688 |
| | | u3 | 42 days LDL ratio | 6 | 107.0369419 | 14.7154796 | 79.8449612 | 121.1009174 |
| Control | 10 | u0 | Baseline LDL | 10 | 100.0000000 | 0 | 100.0000000 | 100.0000000 |
| | | u1 | 7 days LDL ratio | 10 | 93.7350811 | 8.9747121 | 83.7837838 | 107.1428571 |
| | | u2 | 14 days LDL ratio | 8 | 104.5965396 | 13.8625952 | 83.7837838 | 125.2631579 |
| | | u3 | 42 days LDL ratio | 10 | 102.6699920 | 16.2815599 | 77.0270270 | 138.1578947 |

*P < 0.05 when compared to placebo group, student t-test.

Using cohort 1 as reference, it was determined whether CD24Fc reduced LDL-C levels in a dose- and time-dependent manner. As shown in Table 4, compared with cohort 1 which received 10 mg of CD24Fc, a significant dose-dependent reduction of LDL-C levels was observed (p<0.0001).

TABLE 4

Dose and time-dependence of LDL-C reduction in Cohorts by GEE model, using cohort 1 (the lowest dose as reference)

| Parameter | Estimate | Standard Error | 95% Confidence Limits | | Z | Pr > \|Z\| |
|---|---|---|---|---|---|---|
| Intercept | 98.0544 | 5.4745 | 87.3245 | 108.7842 | 17.91 | <.0001 |
| time | 1.6471 | 2.1861 | −—2.6375 | 5.9317 | 0.75 | 0.4512 |
| 30 mg | 3.7167 | 7.3244 | −—10.6389 | 18.0722 | 0.51 | 0.6118 |
| time* 30 mg | −1.4733 | 3.5435 | −—8.4183 | 5.4718 | -0.42 | 0.6776 |

TABLE 4-continued

| | | | | | | |
|---|---|---|---|---|---|---|
| Dose and time-dependence of LDL-C reduction in Cohorts by GEE model, using cohort 1 (the lowest dose as reference) | | | | | | |
| Parameter | Estimate | Standard Error | 95% Confidence Limits | | Z | Pr > \|Z\| |
| 60 mg | ——25.4898 | 14.4124 | ——53.7377 | 2.7581 | ——1.77 | 0.0770 |
| time* 60 mg | 10.7245 | 5.0225 | 0.8805 | 20.5685 | 2.14 | 0.0327 |
| 120 mg | ——21.2684 | 9.4771 | ——39.8431 | ——2.6936 | ——2.24 | 0.0248 |
| time* 120 mg | 6.6669 | 3.9357 | ——1.0468 | 14.3806 | 1.69 | 0.0903 |
| 240 mg | ——15.8681 | 6.9247 | ——29.4402 | ——2.2960 | ——2.29 | 0.0219 |
| time* 240 mg | 5.4390 | 2.8825 | ——0.2106 | 11.0887 | 1.89 | 0.0592 |

A statistically significant dose-dependent reduction of LDL-C was observed, indicating that CD24Fc is effective for lowering LDL-C in human patients.

Figure 9:
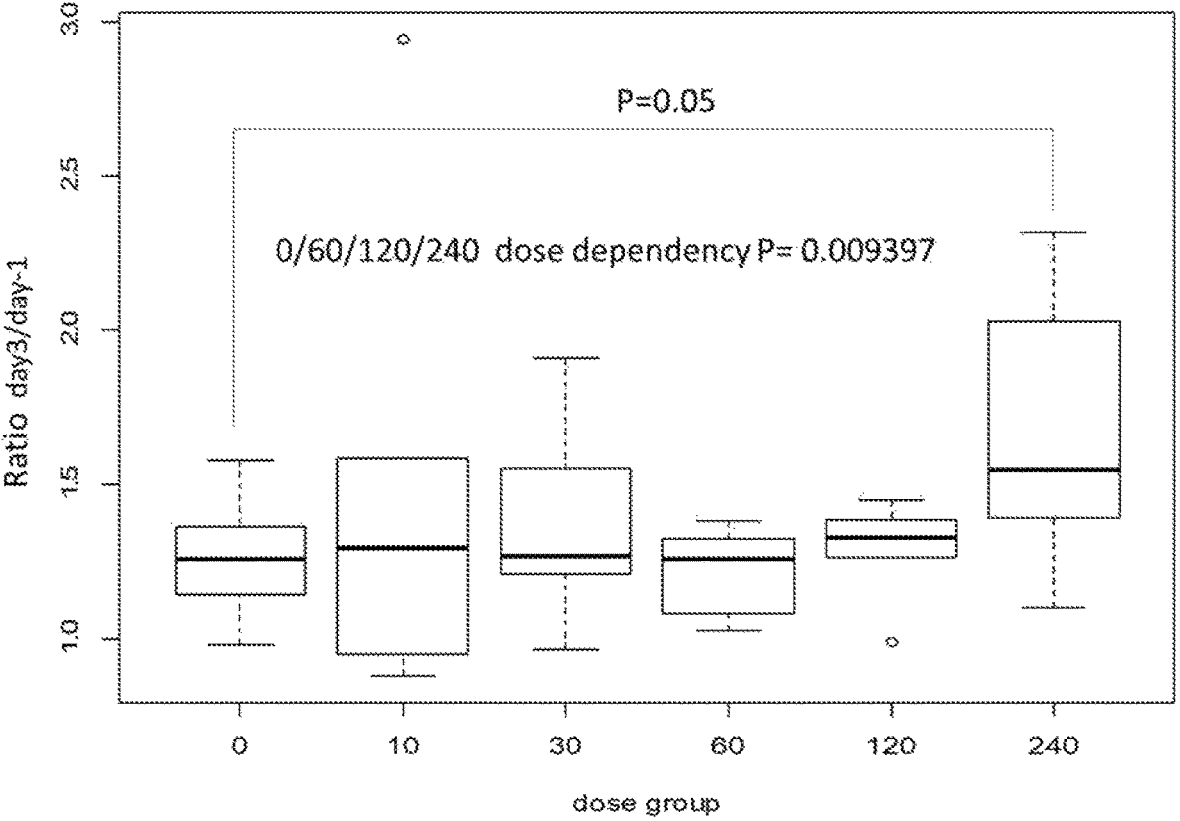
FIG. 9 shows the ratio of leptin on day3/day−1 for patients grouped by dosing cohort. Serum samples (pre-dosing and day 3 after dosing) were taken from Subjects in the Phase I trial involving subjects receiving single CD24Fc doses: 0, 10, 30, 60, 120, 240 mg. The levels of leptin were measured at pre-dosing baseline, and 3 days after dosing. Based on linear regression analysis, dose-dependent induction of leptin was observed in patients receiving placebo, 60, 120 and 240 mg of CD24Fc (P=0.009). When compared with placebo control, 240 mg of CD24Fc significantly induced leptin on day 3 (P=0.05).

Using a Luminex bead-based immunoassay, plasma leptin levels were also measured in samples obtained on Day −1 pre-treatment and Day 3-post treatment from the 40 healthy subjects receiving CD24Fc or placebo. As shown in FIG. 9, there is a upward trend in the relative amount circulating leptin following CD24Fc treatment and between the 0, 60, 120 and 240 mg cohorts this increase is statistically significant (P=0.009397, dose-dependent general linear model regression), demonstrating a dose dependent increase above 60 mg. Furthermore, there is a statistically significant increase in the level of leptin following CD24Fc administration in the 240 mg cohort compared to placebo (0 mg) (P=0.05 as determined by Student's T test), indicating that CD24Fc is effective for increasing leptin in human patients.

Example 5

Global Assessment of CD24Fc Activity on the Host Immune System

Figure 10A:
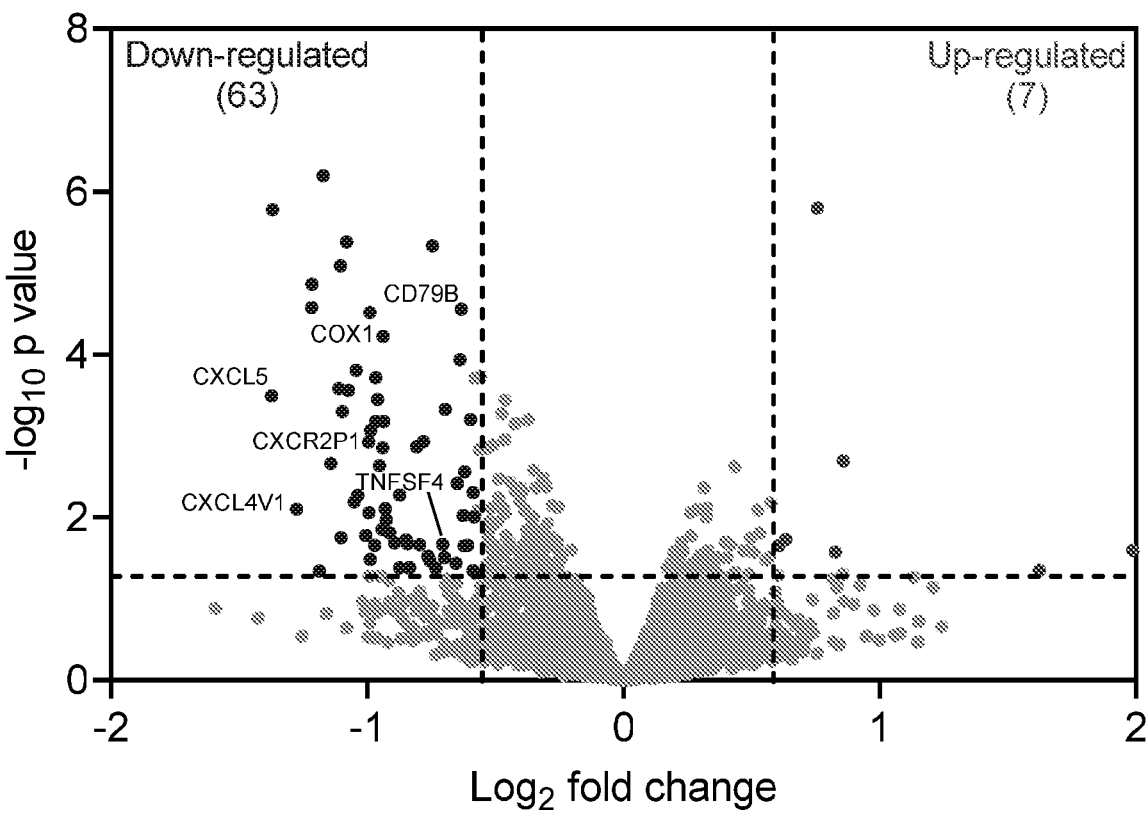
FIGS. 10A-C show that CD24Fc regulates LDL-C levels and expression of inflammatory genes in healthy volunteers. RNA-sequencing was performed on PBMC samples obtained on Day −1 (pre-treatment) and Day 3 (post-treatment) from subjects receiving 240 mg of CD24Fc. All samples that pass quality control were used.
Figure 10B:
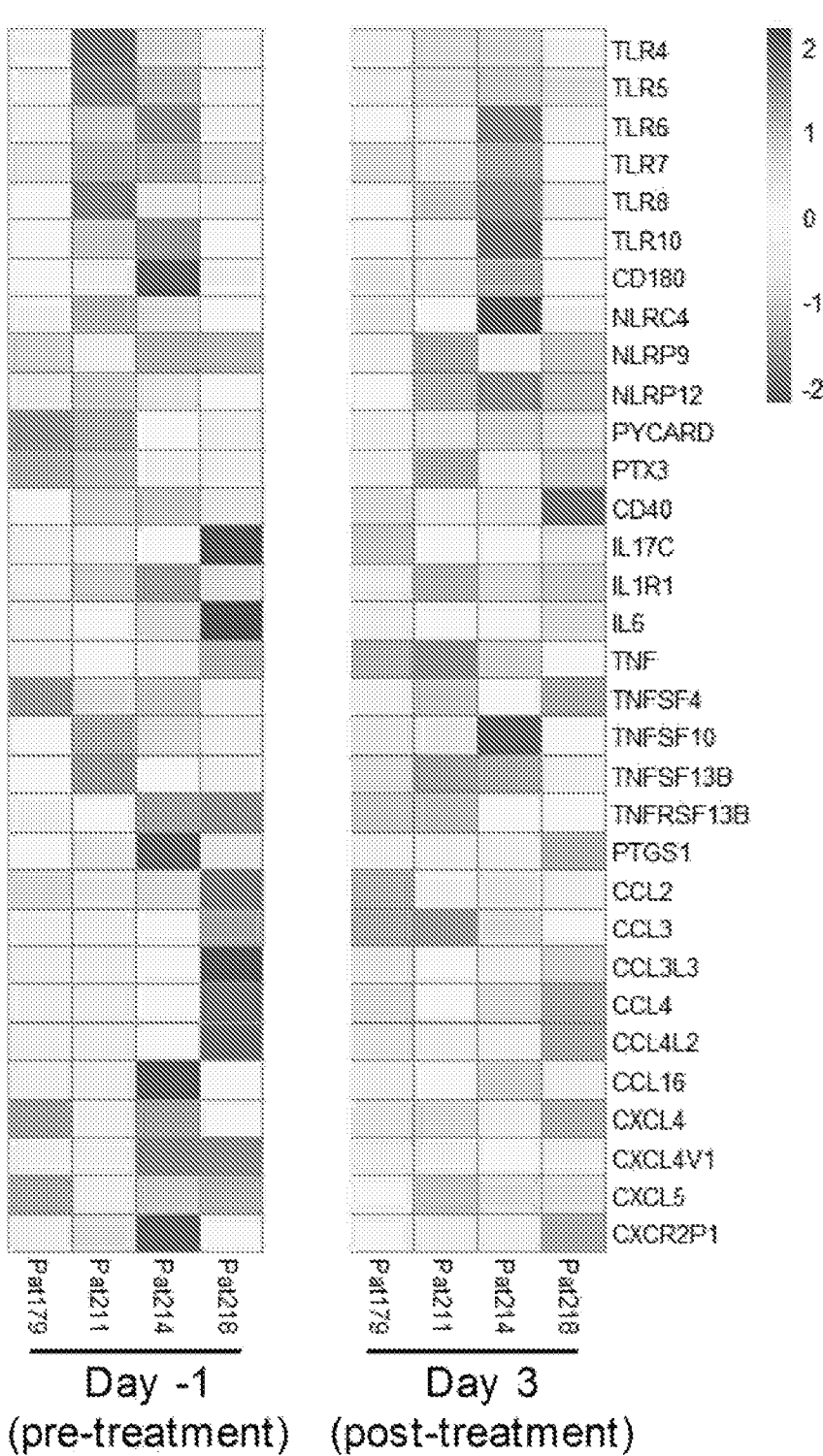
Figure 10C:
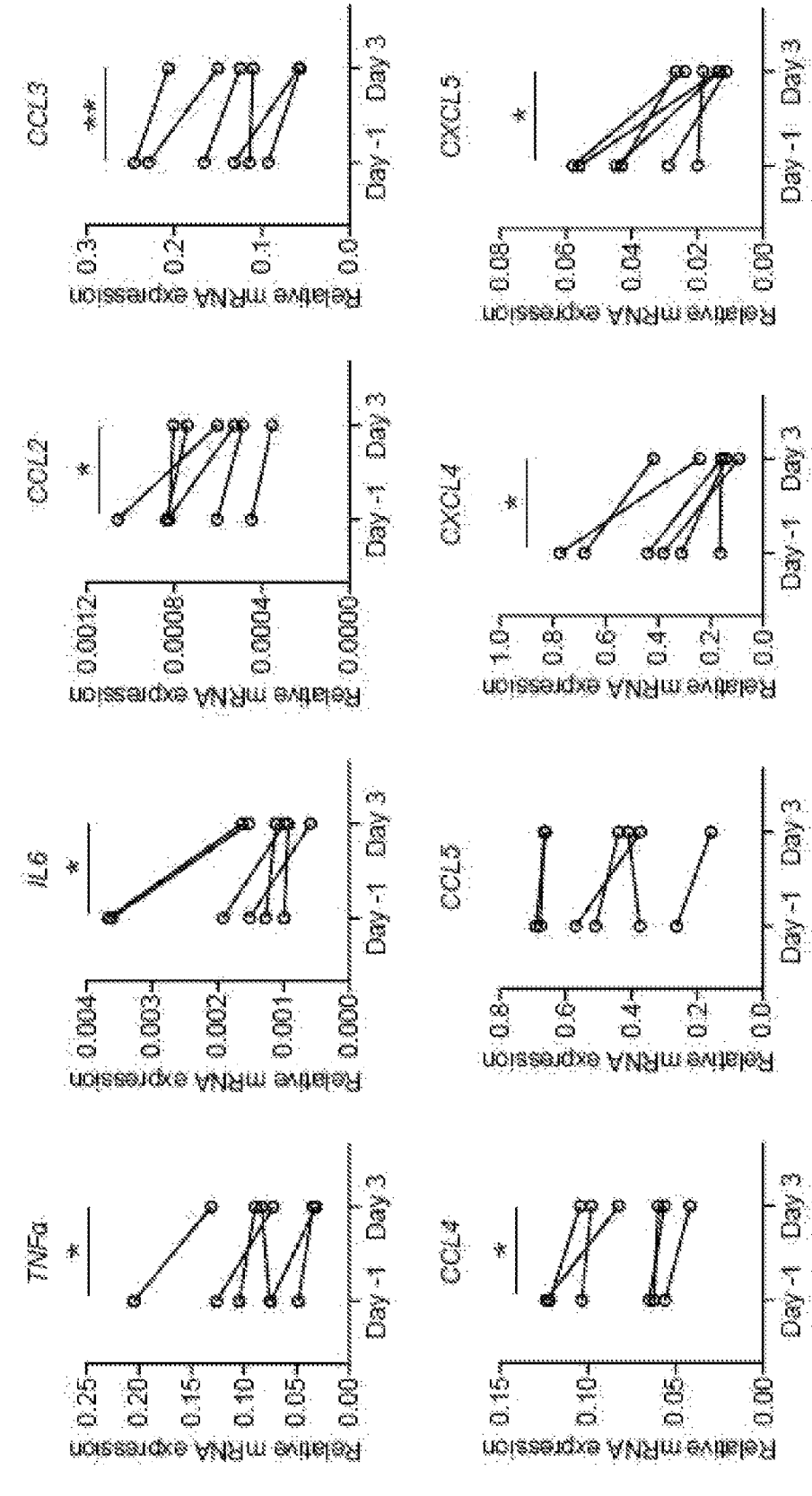

For global assessment of CD24Fc activity on the host immune system, we collected the peripheral blood mononuclear cells (PBMC) from healthy subjects in the CD24Fc Phase I clinical study described above, and performed RNA-sequencing of PBMC samples obtained on Day −1 (pre-treatment) and Day 3 (post-treatment) from subjects receiving 240 mg of CD24Fc. Of the samples collected from 6 patients, 4 pairs of RNA samples passed quality control and were subject to RNA-seq. Using 50% increase or reduction and P<0.05 as the threshold, we identified 7 up-regulated genes and 63 down-regulated genes. The strong bias towards gene down-regulation is consistent with CD24Fc as an inhibitory immune modulator. More importantly, when levels of inflammatory response gene transcripts prior to and 3 days post-dosing were systematically compared, we observed reductions among the transcripts of genes encoding pattern recognition receptors (TLR, NLR, PTX, ASC), as well as inflammatory cytokines and chemokines and their receptors (FIG. 10A and FIG. 10B). To validate the RNA-seq results, we examined the RNA levels of multiple inflammatory cytokines and chemokines by quantitative polymerase chain reaction (qPCR). As shown in FIG. 10C, CD24Fc treatment significantly reduced mRNA levels of inflammatory cytokines (TNFa, IL6) and chemokines (CCL2, CCL3, CCL4, CXCL4 and CXCL5). Taken together, our first-in-human study of CD24Fc not only reveal its safety, but also its biological activities in modulating metabolism and inflammation.

Example 6

CD24Fc Reduces LDL-C Levels Among HCT Patients

To confirm the effect of CD24Fc on LDL-C levels, the effect of CD24Fc on LDL-C levels in hematopoietic cell transplantation (HCT) patients was prospectively tested. This Phase IIa trial (ClinicalTrials.gov Identifier: NCT02663622) was a randomized double blind trial comprising two single ascending dose cohorts (240 mg and 480 mg) and a single multi-dose cohort (480 mg (day −1), 240 mg (day +14) and 240 mg (day +28)) of CD24Fc in addition to SOC for the prevention of acute graft-versus-host disease (GVHD) following myeloablative allogeneic hematopoietic cell transplantation.

Figure 11:
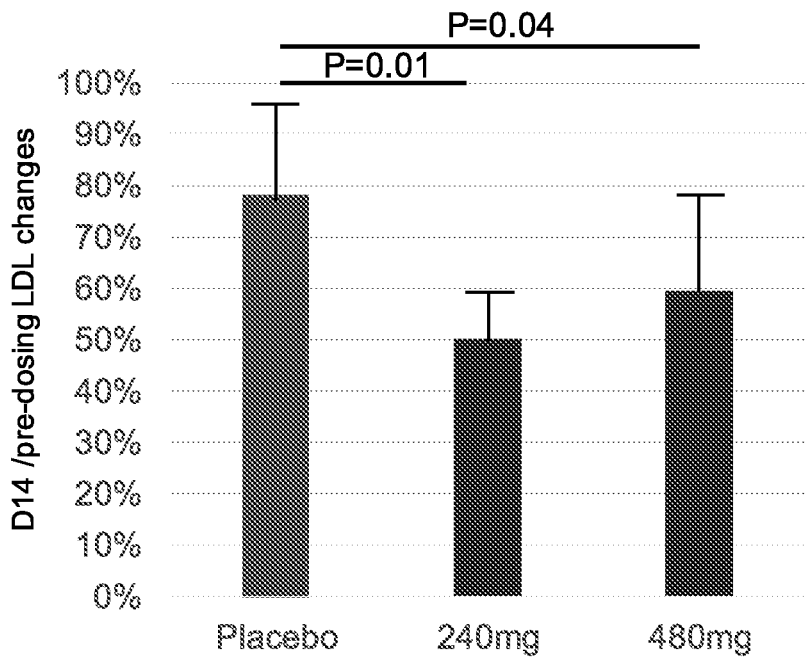
FIG. 11 shows single dosing of CD24Fc reduces LDL-C levels in hematopoietic stem cell transplantation (HCT) patients. The study involved three arms: placebo control (N=6), 240 mg single dosing (N=6) and 480 mg single dosing (N=12, as the samples from multi-dosing cohort patients after receiving the first dosing are included). Data shown are % of pre-dosing LDL-C levels at 14 days after HCT (15 days after CD24Fc or placebo dosing). Statistical significance (P values) was calculated by two tailed t-tests.

As shown in FIG. 11, at 15 days after doing of placebo, HCT patients had approximately 80% of the pre-dosing levels of LDL-C. This level was reduced to 50% and 60%, respectively, among patients receiving 240 mg (P=0.01) or 480 mg (P=0.04). The significant reductions confirm the activity of CD24Fc in reducing LDL-C in human.

Example 7

CD24Fc Alleviates Obesity-Related Metabolic Disorders in DIO Mice

Figure 12D:
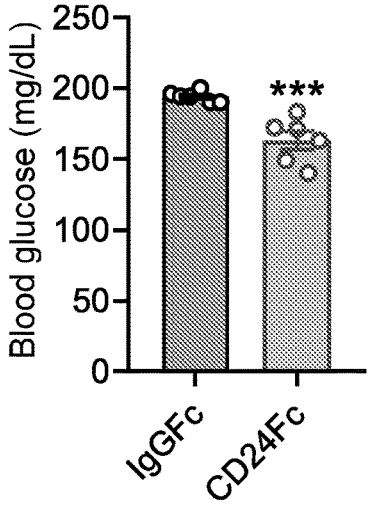
FIG. 12D. Fasting blood glucose. n=6 per group.
Figure 12E:
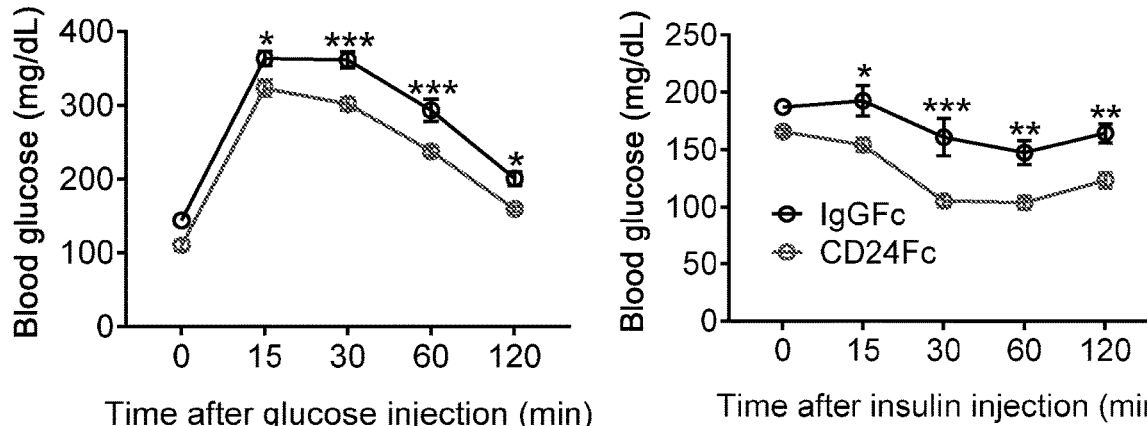
FIG. 12E. GTT and ITT data for mice on HFD. n=8-10 per group.

To substantiate the surprising observation of CD24Fc in metabolic modulation, we tested the effects of CD24Fc treatment in diet-induced obese (DIO) mice. We challenged wild-type mice with a high-fat diet (HFD) and concurrently treated mice with CD24Fc or IgGFc control for 8 weeks and assessed their metabolic parameters. As shown in FIG. 12A, CD24Fc treatment significantly reduced the rate of body weight gain under HFD. The reduction was selective for fat content (FIG. 12B). Consistent with its effect on lipid metabolism in humans, CD24Fc treatment significantly decreased total cholesterol (TC), triglycerides (TG), LDL-C and free fatty acid (FFA) levels, while increasing HDL-C levels (FIG. 12C). Fasting blood glucose levels were also reduced (FIG. 12D). In addition, CD24Fc treatment alleviated glucose intolerance and insulin resistance as revealed by glucose tolerance tests (GTT) and insulin tolerance tests (ITT) (FIG. 12E). Improved insulin sensitivity was further supported by increased Akt phosphorylation in the livers from CD24Fc-treated DIO mice after insulin challenge (FIG. 12F).

Chronic exposure to HFD causes moderate non-alcoholic steatosis hepatitis (NASH), with hepatic steatosis, inflammation and mild fibrosis. As shown in FIG. 12G, lipid accumulation was largely alleviated by treatment with CD24Fc, as revealed by H&E staining. Consistent with liver steatosis data, hepatomegaly observed in DIO mice was largely prevented by CD24Fc treatment (FIG. 12H).

Figure 12I:
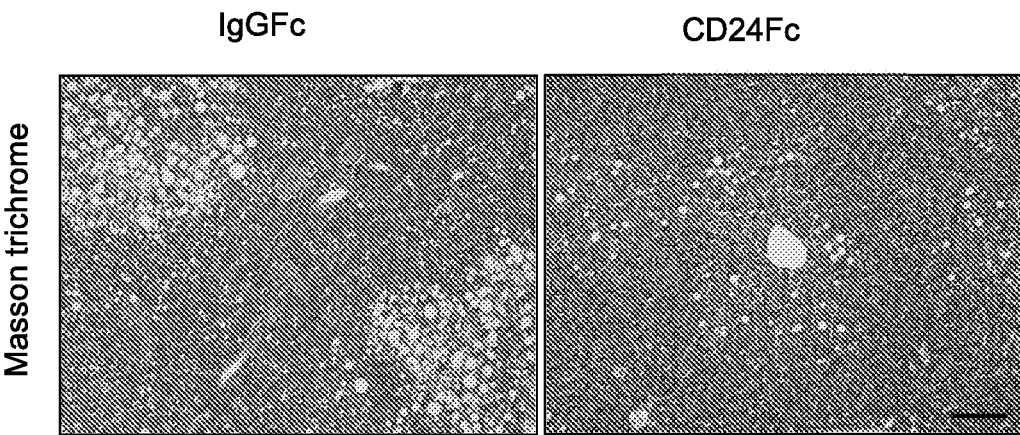
FIG. 12I. Representative images of Masson trichrome stained sections from liver in the groups indicated. Scale bars=100 µm.
Figure 12J:
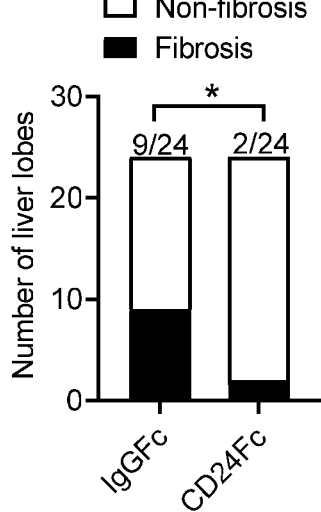
FIG. 12J. Hepatic fibrosis lesions were measured in four liver lobes for each mouse. Data shown are number of lobes with or without fibrosis over 24 lobes examined per group of 6 mice each.

Liver fibrosis, a prominent feature in human NASH, is present but generally mild in HFD-fed mice. However, we still found that CD24Fc treatment significantly alleviated the modest hepatic fibrosis induced by HFD feeding as determined by Masson staining (FIG. 12I). As shown in FIG. 12J, when hepatic fibrosis was measured in 4 liver lobes for each mouse, 9/24 liver lobes with modest fibrosis were observed in 6 mice in IgGFc control group, whereas only 2/24 lobes with fibrosis were observed in the 6 mice in CD24Fc treatment group (P<0.05).

Figure 12K:
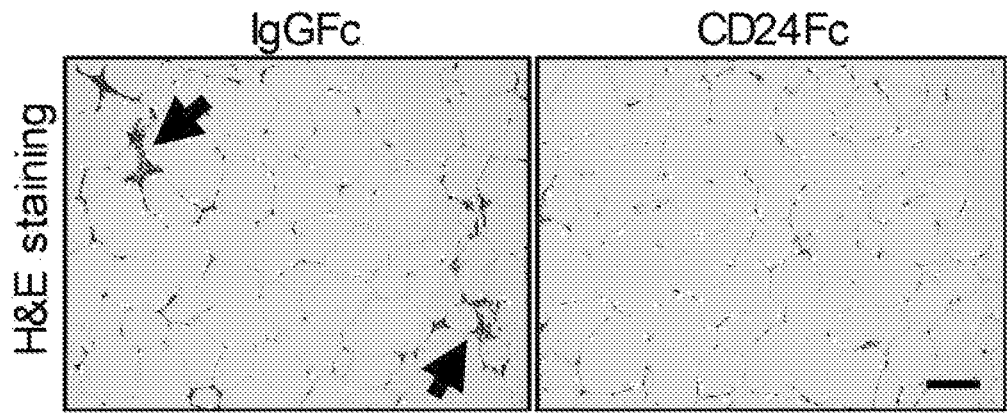
FIG. 12K. Representative images of H&E stained sections from the eWAT in the groups indicated. Arrows indicate inflammatory cells infiltration. Scale bars=100 µm.

Immune cell infiltrates, another key hallmark of NASH, were markedly decreased in liver and adipose tissues in CD24Fc-treated mice compared to IgGFc-treated controls, as assessed by H&E staining (FIGS. 12G and 12K). This reduction of macrophages in crown-like structures in epididymal white adipose tissue (eWAT) was confirmed by flow cytometry (FIG. 12L). Consistently, there was a significant attenuation in the levels of mRNAs encoding key inflammatory cytokines in liver and adipose tissues in CD24Fc-treated mice, including Tnfa, Il6, Il1b, Mcp1, Mip1a and Rantes (FIG. 12M). These data demonstrate that CD24Fc treatment prevents all major features of NASH induced by HFD.

Figure 13A:
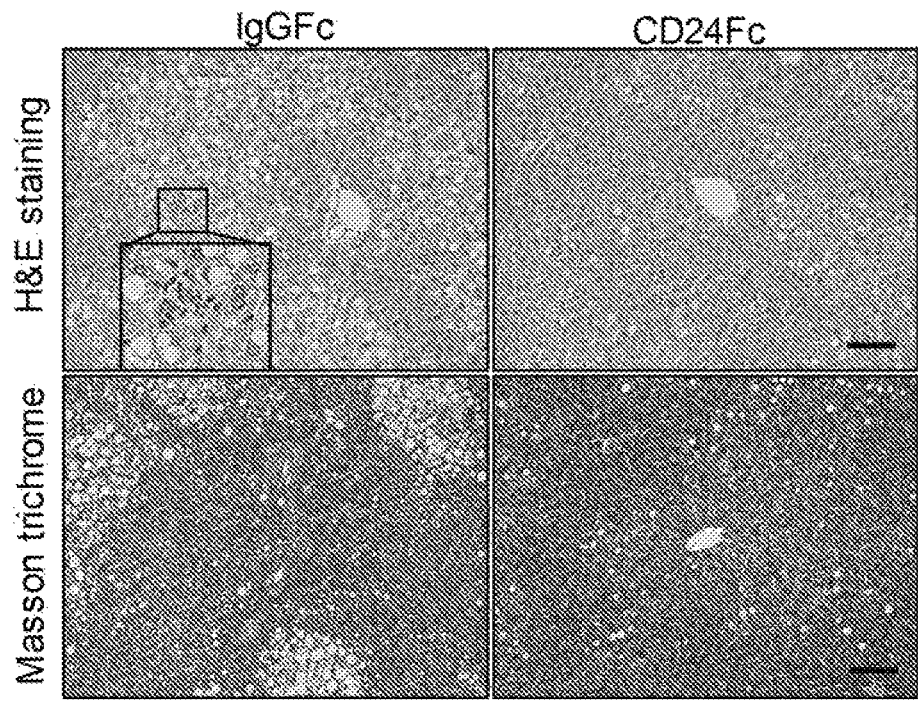
FIGS. 13A-D show that CD24Fc therapy improves NASH in DIO mice. Male C57/BL6/NCr mice were fed with HFD for 8 weeks, then treated with CD24Fc (100 µg per dose) or control IgGFc twice a week for 4 more weeks. n=7 per group.
Figure 13B:
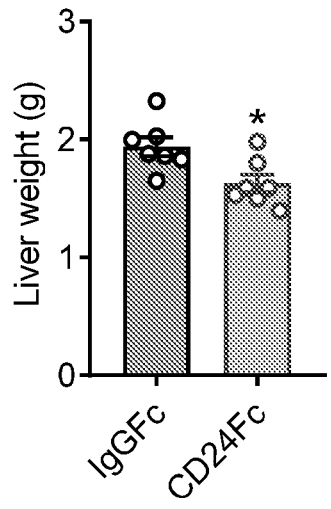
Figure 13C:
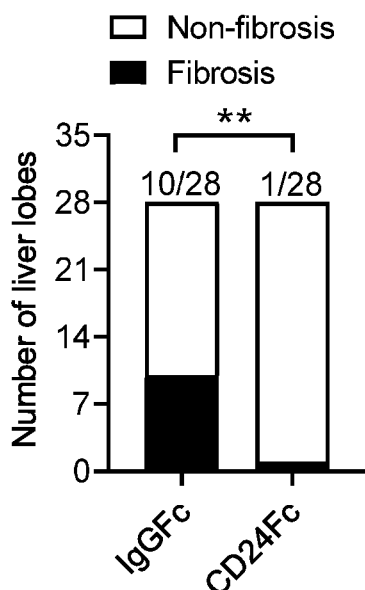
Figure 13D:
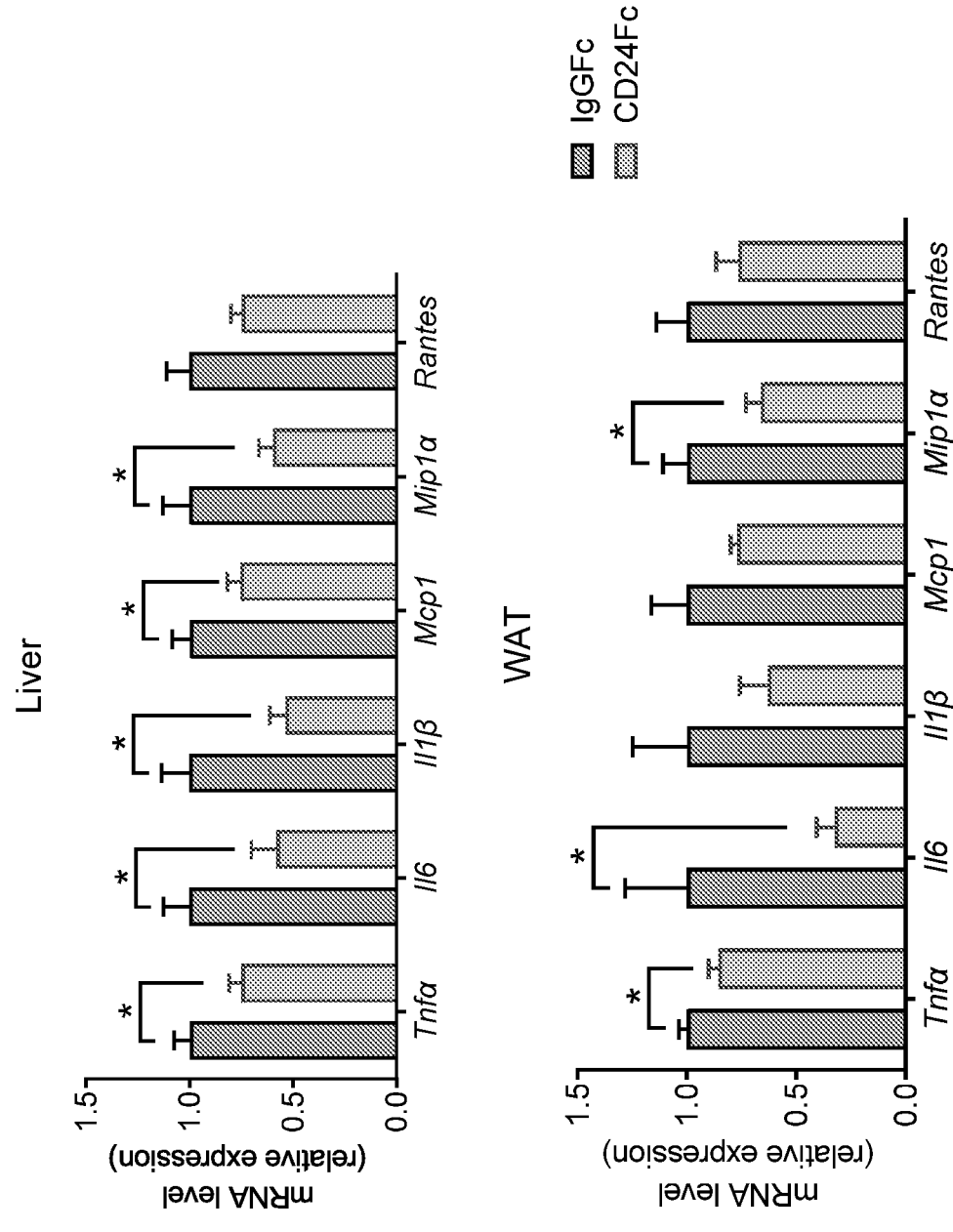

To test the therapeutic effect in obese mice, we administered DIO mice with CD24Fc or IgGFc control for 4 weeks after obesity was established and then tested the metabolic parameters. CD24Fc therapy produced marked improvements in hepatic steatosis, as indicated by reduced liver weight, lipid accumulation and inflammatory cell infiltration (FIGS. 13A and B). Moreover, the modest hepatic fibrosis induced by the HFD was largely alleviated after CD24Fc therapy (FIGS. 13A and C). Consistent with reduced inflammatory cell infiltration, the expression of inflammatory genes in the liver and adipose tissues significantly decreased after CD24Fc treatment (FIG. 13D).

In contrast to the data from the first-in-human study, we did not observe induction of leptin by CD24Fc in DIO mice (data not shown). Consistent with this observation, we found no effect of CD24Fc on mouse food intake (data not shown). These data suggest that the effect on lipid metabolism was not due to its induction of leptin. To substantiate this hypothesis, we treated Leptin-deficient ob/ob mice with CD24Fc or IgGFc control and monitored their body weight and metabolic parameters. Although CD24Fc failed to decrease body weight of the ob/ob mice, it reduced fasting blood glucose, TC and LDL-C levels (FIGS. 14A-D). These data demonstrate that CD24Fc activity on leptin and lipid metabolism in human may be independent of each other. Moreover, CD24Fc may modulate lipid metabolism even if leptin signaling is abnormal as is the case for human obesity.

Methods

Mice and diets: Siglecg and Siglece$^{-/-}$ C57BL/6 mice have been described (Nielsen et al., 1997). All strains were backcrossed with C57BL/6 mice for 6 or more generations. We used age- and sex-matched littermates or wild type C57BL/6 mice as controls. Leptin-deficient (ob/ob) mice were purchased from The Jackson Laboratory. All the mice were maintained at constant temperature (23±2° C.) with a 12-hour light/12-hour dark cycle and given free access to food and water prior to our study. For metabolic studies, Siglec-deficient and WT male mice were fed with HFD consisting of 60% of calories from fat (D12492, Research Diets Inc.) starting at 8-10 weeks of age for 12 weeks. Mouse body weight and food intake were measured every week.

CD24Fc protein therapeutic studies in DIO mice: WT, Siglece$^{-/-}$ or ob/ob mice were injected intraperitoneally with CD24Fc (100 μg per dose, Oncolmmune Inc.) or an equivalent amount of control IgGFc twice a week. Fasting blood glucose and lipid profiles were detected after CD24Fc or IgG treatment. For the prevention groups, CD24Fc administration was begun concurrently with HFD feeding at 8 weeks of age for 8 weeks. For the therapy groups, CD24Fc treatment was performed in mice with established obesity (8 weeks of HFD) for 4 more weeks.

Tissue processing and histological analyses: After HFD treatment, DIO mice were anesthetized with isoflurane. Representative images of their physical appearance were taken and body composition was detected by dual energy X-ray absorptiometry (DEXA). The mice were then euthanized, livers, white adipose and brown adipose tissues were immediately harvested, photographed and weighed. For histology, the tissues were fixed in 10% formalin and embedded in paraffin. The tissues were then cut into 5 μm sections and stained with hematoxylin-eosin (H&E). Liver sections were stained with Mason's Trichrome for fibrosis studies.

Metabolic studies: For the glucose tolerance tests (GTTs), mice were injected intraperitoneally with 1 g/kg glucose (Sigma) after 12 hrs of fasting. Blood glucose levels were measured at 0, 15, 30, 60 and 120 min from tail blood using the One Touch Ultra glucometer (Lifescan). For the insulin tolerance tests (ITTs), an intraperitoneal injection of 1 U/kg insulin (Sigma) was given to mice after 6 hrs of fasting. Blood glucose levels were determined as described above. The serum TC, TG, HDL-C, LDL-C and NEFA levels were measured with commercial kits (Randox). Serum cytokines were determined using mouse cytokine bead array designed for inflammatory cytokines (BD Biosciences).

Insulin sensitivity study: For examination of in vivo insulin signaling, mice were fasted overnight and followed with an intraperitoneal injection of insulin (1 U/kg). Liver were harvested and snap-frozen in RIPA buffer 10 min after injection for phospho-Akt analysis.

Macrophages culture and stimulation: Peritoneal macrophages from WT and Siglece$^{-/-}$ mice were isolated 3 days after intraperitoneal injection of 3% thioglycollate (Sigma). The cells were plated in 6-well plates at a density of 1.2×106 cells/well and cultured in RPMI medium containing 10% fetal bovine serum (FBS). The cells were then stimulated with palmitate-bovine serum albumin (BSA) or unmodified BSA control (500 μM) for 16 h. For CD24Fc treatment studies, peritoneal macrophages from WT and Siglece$^{-/-}$ mice were challenged with palmitate-BSA or BSA control (500 μM) and concurrently treated with CD24Fc (10 μg/ml) or IgG control for 16 hours. Supernatant and cell lysate were collected for ELISA, immunoblot and gene expression analysis. Palmitate (Sigma) was conjugated with BSA before treatment. Palmitate was dissolved in 95% ethanol at 60° C. and prepared as a 50 mM solution. The palmitate solution was then diluted with RPMI medium containing 1% BSA to obtain the 500 μM palmitate concentration.

RNA extraction and Real-time PCR analysis: Total RNA was isolated from tissues and cells using TRIzol reagent (Invitrogen). For reverse transcription, cDNA was synthesized from RNA samples with a Superscript First-Strand Synthesis System (Invitrogen). Quantitative real-time PCR was performed with SYBR Green PCR Master Mix (Applied Biosystems) using the Applied Biosystems 7500 Real-time PCR System according to the manufacturer's instructions. Gene expression levels were calculated after normalization to the housekeeping gene β-actin or GAPDH.

Western blot: Tissues and cells were lysed with RIPA lysis buffer (Thermo) containing protease inhibitor (Sigma) and phosphatase inhibitor (Sigma). Total protein was quantified by BCA assay (Thermo). Equal amounts of each protein sample were electrophoresed on NuPAGE 4-12% Bis-Tris Protein Gels (Life Technologies) and transferred to PVDF membranes (Millipore). Individual proteins were determined with the specific antibodies and actin was used as an internal loading control.

Immunoprecipitation: The spleens of the indicated mice (8-10 weeks) were collected, sliced and pressed through the strainer to get single cells. The red blood cells were removed using the ACK buffer (Thermo). Then the spleen cell lysates were prepared in the buffer B (1% Triton X-100, 150 mM NaCl, 3 mM MnCl2, 1 mM CaCl2, 1 mM MgCl2, 25 mM Tris-HCl, pH 7.6) with protease inhibitor cocktail (Sigma) for immunoprecipitation or western blot. For immunoprecipitation, cell lysates were pre-cleared with Protein A/G-conjugated agarose beads (Santa Cruz) at 4° C. for 2 hours with rotation, then incubated with anti-CD24 antibody (M1/69, Biolegend) or control Rat anti-IgG (Santa Cruz) overnight at 4° C. The cell lysates were then incubated with Protein A/G-conjugated agarose beads for an additional 2 hours. The beads were washed four times with buffer B and re-suspended in SDS sample buffer (non-reducing condition) for western blot analysis.

Immunofluorescence: For immunofluorescence staining, livers were embedded in OCT compound and frozen at −80° C. The tissues were then cut into 7 μm sections using a cryostat. For peritoneal macrophages, cells were seeded on chamber slides (Thermo). The slides were washed in PBS, fixed in 4% fresh paraformaldehyde for 15 min, permeabilized with 0.5% Triton X-100 in PBS for 5 min and blocked with 3% BSA in PBS for 60 min at room temperature. The slides were then stained with NF-κB/p65 antibody (Cell Signaling Technology) in PBS overnight at 4° C. After washing with PBST for 3 times, the slides were incubated with Alexa Fluor 594-conjugated goat anti-rabbit (Life technology) for 60 min at room temperature. Nuclei were stained with DAPI for 5 min. Fluorescent images were obtained using a fluorescent microscope.

Flow cytometry: eWAT was removed, weighed, finely minced and then digested in 2 ml DMEM medium containing Collagenase Type II (1 mg/ml) at 37° C. for 30 min with 150 rotations per minute. The cell suspension was diluted by 10× volume of DMEM medium and passed through a 100 μm cell stainer. After centrifuging at 400 g for 5 min and washing twice, cells were blocked with anti-FcR (2.4 G2, 5 mg/ml) for 10 min and incubated with the indicated Abs for 30 min at 4° C. Counting beads (Invitrogen, 123count eBeads™) were added to calculate the absolute cell number before running flow cytometry. The samples were analyzed by the BD Canton II Flow cytometer and data were analyzed by FlowJo software.

Statistical analysis: The specific tests used to analyze each set of experiments are indicated in the figure legends. Data were analyzed using an unpaired two-tailed Student's t test to compare between two groups, one-way analysis of variance (ANOVA) for multiple comparisons, two-way ANOVA for body weight, GTT and ITT data that were repeatedly measured. All statistical tests were performed using Graph- Pad Prism (GraphPad Software, San Diego, California), and P<0.05 was considered statistically significant.

Example 8

Siglec-E is the CD24 Receptor that Controls Metabolic Programming in Mice

Figure 15A:
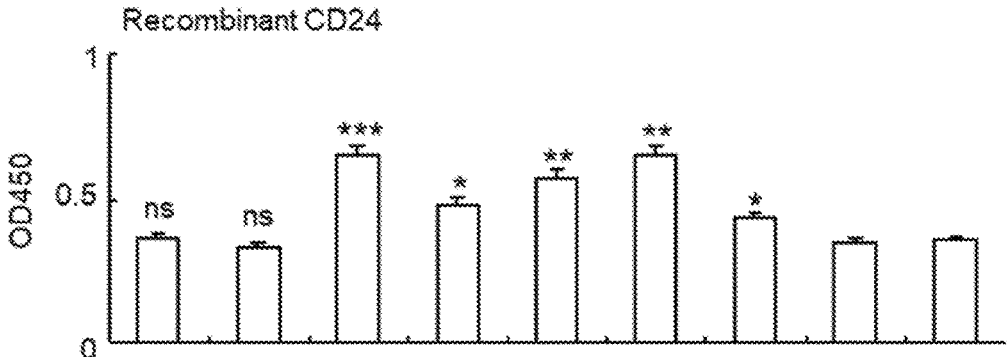
FIGS. 15A-B show that Siglec-E is a CD24 receptor and controls metabolic programming in mice.
Figure 15B:
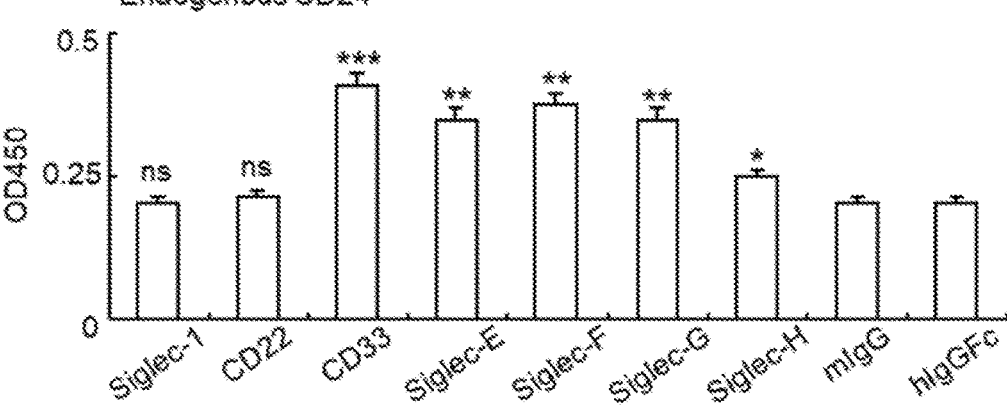

Sialoside-based pattern recognition is mediated by interaction between Siglecs and sialic acid-containing glycoproteins. CD24 is a highly sialylated glycosyl-phosphatidylinositol (GPI)-anchored cell surface protein without an intracellular domain. Therefore, we hypothesize that CD24 mediates metabolic programming by interacting with Siglecs. To test this hypothesis, we first evaluated the specificity of the CD24-Siglec interactions using capture ELISA. We compared mouse Siglec fusion proteins for their binding to CD24 on spleen cells. As shown in FIG. 15B, there was a significant interaction between endogenous CD24 and CD33, Siglec-E, Siglec-F, Siglec-G, and to a less extent Siglec-H, but not Siglecs-1 and CD22. To test if CD24 directly interacts with Siglecs, we used recombinant human CD24Fc in an ELISA binding assay, and observed a similar pattern of interaction between CD24Fc and recombinant Siglecs (FIG. 15A).

Figure 16:
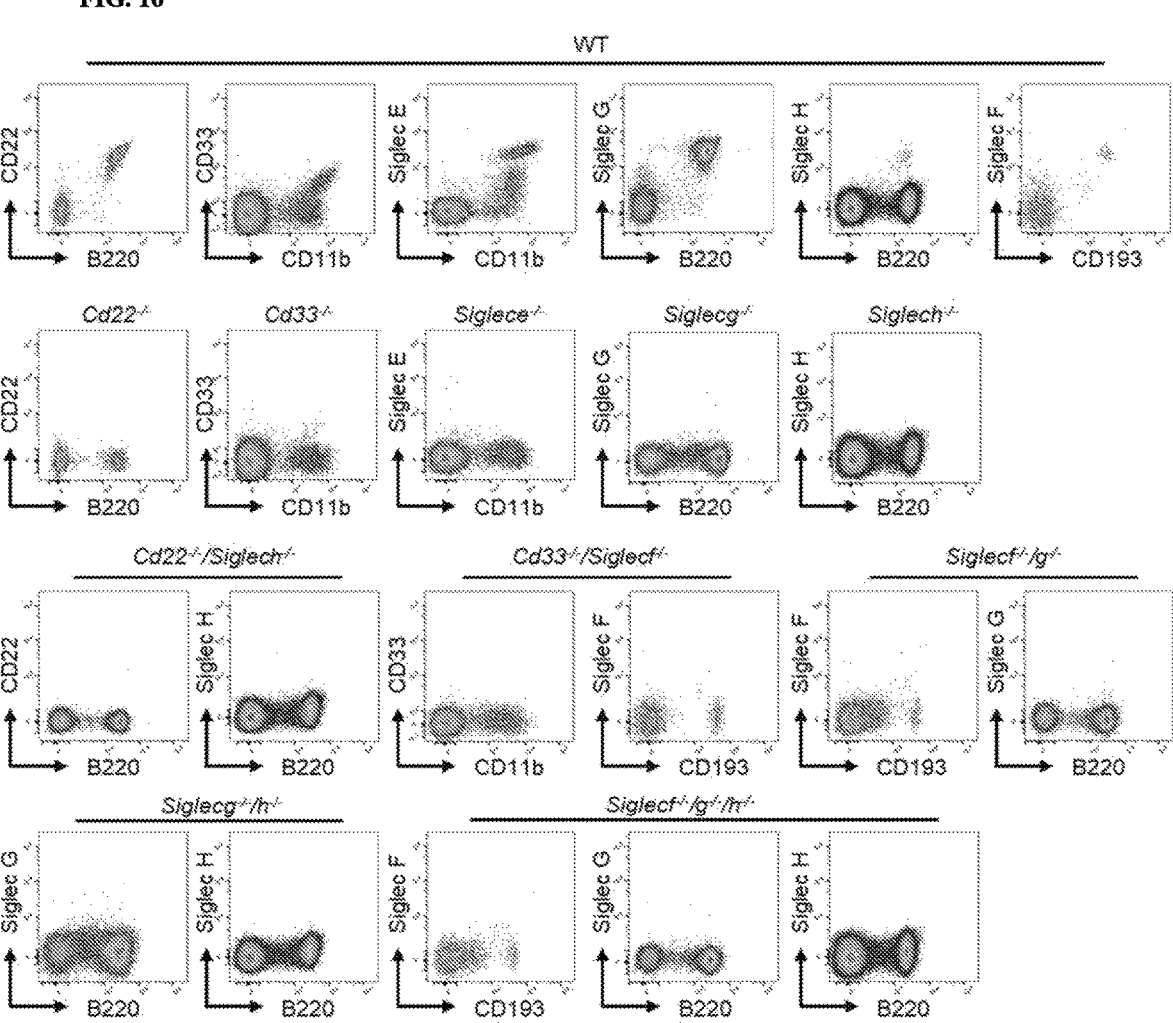
FIG. 16 shows Siglecs mutations abrogate their cell surface expression, related to FIG. 4. Siglec mutations were confirmed by flow cytometry of indicated strains. X-axis represents cell population and Y-axis represents Siglec expression.

To identify the CD24 receptor responsible for metabolic homeostasis, we took a genetic approach determine whether the mutation in any Siglec gene may recapitulate the metabolic phenotype of Cd24 mutation. In addition to mice with mutations of either the Siglecg and Siglece genes that we have previously reported (Ding et al., 2007; Flores et al., 2019), we produced mice with mutations of one or more of the additional Siglec genes (FIG. 16).
Methods
As described in Example 7.

Example 9

CD24Fc Improves Metabolic Syndrome Through Siglec-E

Figure 17A:
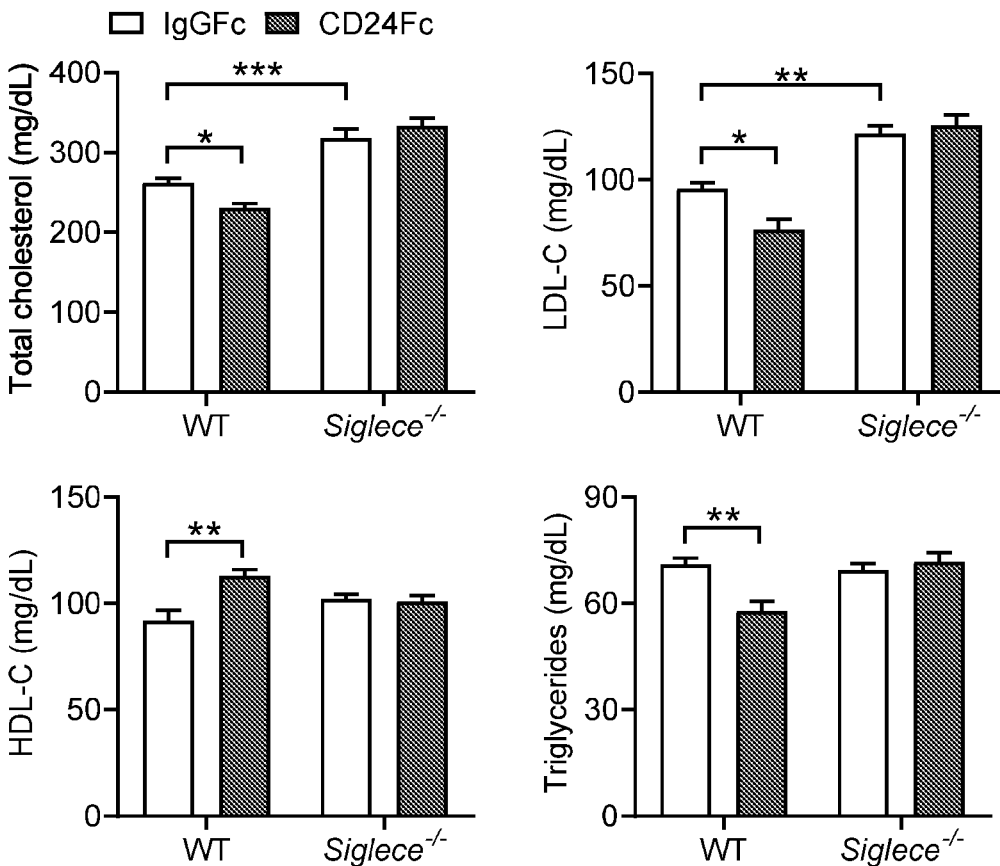
Figure 17B:
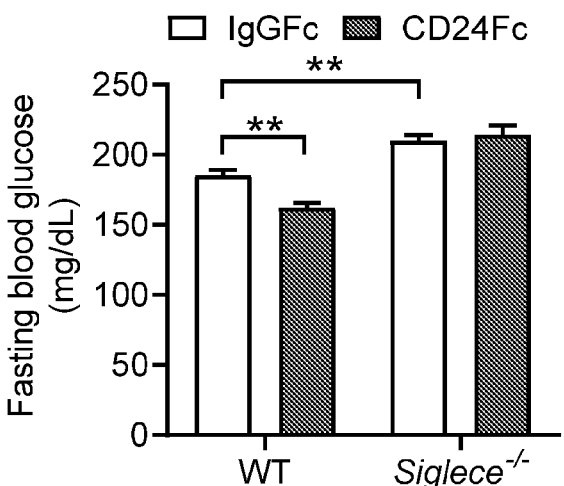
Figures 17E, 17F:
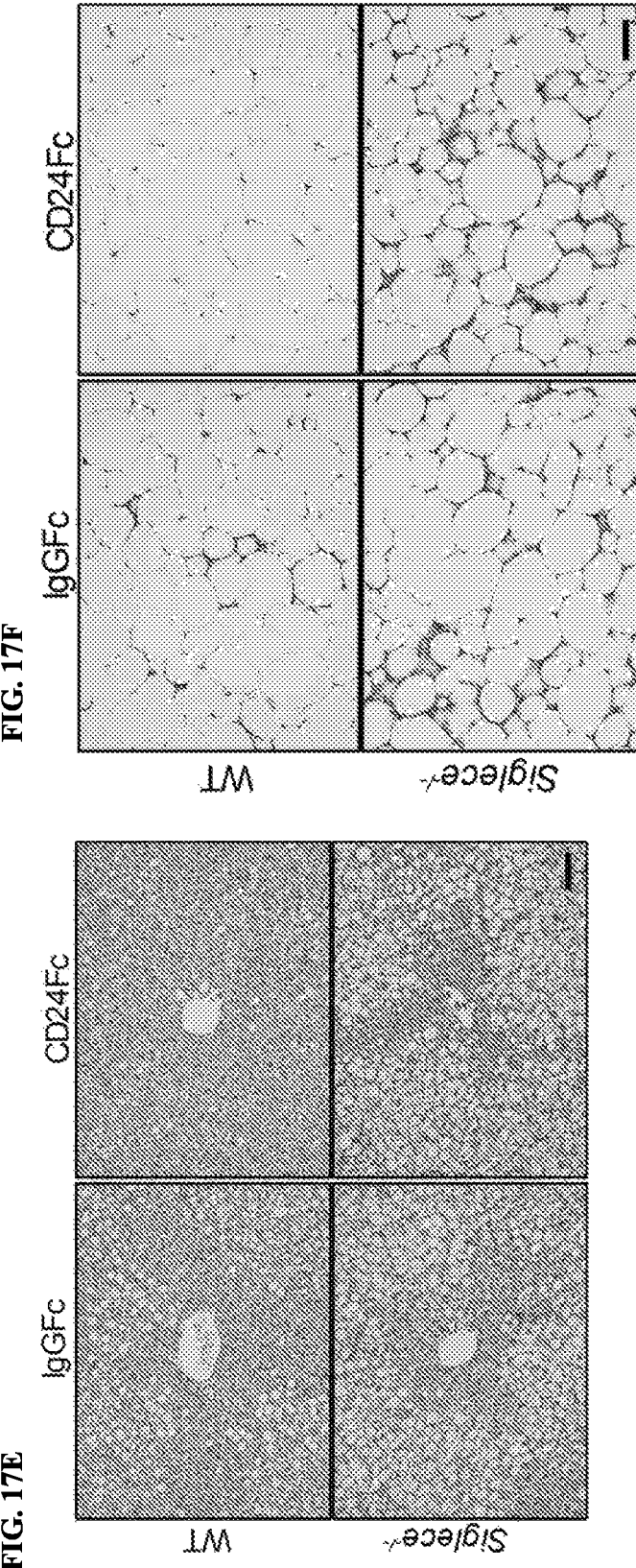

To evaluate whether CD24 improves metabolic disorders through Siglec-E, we compared WT and Siglece$^{-/-}$ mice with established obesity for their response to the therapeutic effect of CD24Fc. CD24Fc treatment improved fasting blood glucose and lipid profiles in WT but not Siglece$^{-/-}$ mice (FIGS. 17A and 17B). We also monitored glucose tolerance and insulin sensitivity by GTT and ITT tests. Treatment of WT mice with CD24Fc produced an improvement in glucose tolerance and insulin sensitivity. However, the therapeutic effects were absent in Siglece$^{-/-}$ mice (FIG. 17C). In addition, CD24Fc therapy produced significant improvements in hepatomegaly and steatosis in WT mice after HFD feeding, but not in Siglece$^{-/-}$ mice (FIGS. 17D and E). Moreover, immune cell infiltrates, indicated as crown-like structures, were markedly decreased in adipose tissue in CD24Fc-treated WT mice, but not in Siglece mice, as assessed by H&E staining (FIG. 17F). These data demonstrate that the therapeutic function of CD24Fc for metabolic syndrome is mediated specifically through Siglec-E.

Figure 18D:
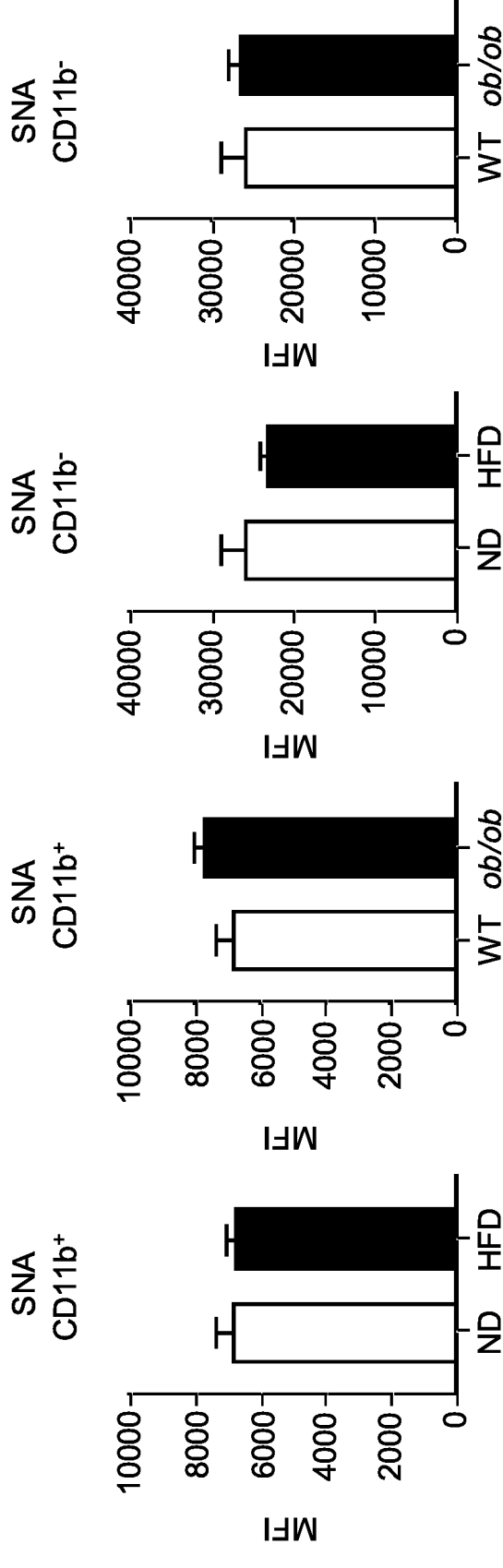

One mechanism to disable sialoside-based pattern recognition is desialylation. Consistent with clinical observations in obese patients and those with abnormal lipid and glucose metabolism (Browning et al., 2004; Rajappa et al., 2013; Yerlikaya et al., 2015), we observed significant increases in free sialic acid (SA) levels in the plasma of both DIO mice and ob/ob mice (FIG. 18A). The total SA also decreased in ob/ob mice (FIG. 18B). Consistent with the increased free SA level, we observed a corresponding reduction of global sialylation on immune cells of PBMC from DIO mice and ob/ob mice, as revealed by MAL H lectins that recognize α2-3-linked sialic acids, although SNA-binding α2-6-linked sialic acids was unaffected (FIGS. 18C and D). These results are consistent with the notion that defects in sialoside-based pattern recognition as a potential underlying cause of metabolic disorders observed in the mouse model.

Methods

As described in Example 7.

---

The invention claimed is:

1. A method of treating nonviral hepatitis in a subject in need thereof, comprising administering a CD24 protein to the subject.

2. The method of claim 1, wherein the CD24 protein comprises a mature human CD24 polypeptide.

3. The method of claim 2, wherein the mature human CD24 polypeptide comprises the sequence set forth in SEQ ID NO: 1 or 2.

4. The method of claim 3, wherein the CD24 protein comprises a Fc region of a mammalian Ig protein fused at the N-terminus or C-terminus of the CD24 protein.

5. The method of claim 4, wherein the Ig protein is a human Ig protein.

6. The method of claim 5, wherein the Fc region comprises the hinge region and CH2 and CH3 domains of IgG1, IgG2, IgG3, IgG4, or IgA.

7. The method of claim 6, wherein the CD24 protein comprises the sequence set forth in SEQ ID NO: 6, 11, or 12.

8. The method of claim 7, wherein the amino acid sequence of the CD24 protein consists of the sequence set forth in SEQ ID NO: 6, 11, or 12.

9. The method of claim 5, wherein the Fc region comprises the hinge region and CH2, CH3 and CH4 domains of IgM.

10. The method of claim 1, wherein the CD24 protein is soluble.

11. The method of claim 1, wherein the CD24 protein is glycosylated.

12. A method of treating liver fibrosis in a subject in need thereof, wherein the subject does not have a history of excessive alcohol use, comprising administering a CD24 protein to the subject.

13. The method of claim 12, wherein the CD24 protein comprises a mature human CD24 polypeptide.

14. The method of claim 13, wherein the mature human CD24 polypeptide comprises the sequence set forth in SEQ ID NO: 1 or 2.

15. The method of claim 14, wherein the CD24 protein comprises a Fc region of a mammalian Ig protein fused at the N-terminus or C-terminus of the CD24 protein.

16. The method of claim 15, wherein the Ig protein is a human Ig protein.

17. The method of claim 16, wherein the Fc region comprises the hinge region and CH2 and CH3 domains of IgG1, IgG2, IgG3, IgG4, or IgA.

18. The method of claim 17, wherein the CD24 protein comprises the sequence set forth in SEQ ID NO: 6, 11, or 12.

19. The method of claim 18, wherein the amino acid sequence of the CD24 protein consists of the sequence set forth in SEQ ID NO: 6, 11, or 12.

20. The method of claim 16, wherein the Fc region comprises the hinge region and CH2, CH3 and CH4 domains of IgM.

21. The method of claim 12, wherein the CD24 protein is soluble.

22. The method of claim 12, wherein the CD24 protein is glycosylated.

* * * * *